(12) United States Patent
Diamond

(10) Patent No.: US 8,933,405 B2
(45) Date of Patent: Jan. 13, 2015

(54) INSPECTION APPARATUS AND METHOD

(75) Inventor: Geoffrey Graham Diamond, Warwickshire (GB)

(73) Assignee: Inspection Technologies Limited (GB)

( * ) Notice: Subject to any disclaimer, the term of this patent is extended or adjusted under 35 U.S.C. 154(b) by 259 days.

(21) Appl. No.: 13/637,669

(22) PCT Filed: Mar. 29, 2011

(86) PCT No.: PCT/GB2011/050643
§ 371 (c)(1),
(2), (4) Date: Sep. 27, 2012

(87) PCT Pub. No.: WO2011/121346
PCT Pub. Date: Oct. 6, 2011

(65) Prior Publication Data
US 2013/0015354 A1    Jan. 17, 2013

(30) Foreign Application Priority Data

| Mar. 29, 2010 | (GB) | 1005156.3 |
| Mar. 29, 2010 | (GB) | 1005157.1 |
| May 4, 2010 | (GB) | 1007408.6 |
| Jun. 22, 2010 | (GB) | 1010484.2 |
| Jun. 24, 2010 | (GB) | 1010650.8 |
| Nov. 18, 2010 | (GB) | 1019544.4 |

(51) Int. Cl.
*G01J 5/02* (2006.01)
*G01N 21/47* (2006.01)

(52) U.S. Cl.
CPC ................. *G01N 21/4795* (2013.01)
USPC .................................... 250/339.07

(58) Field of Classification Search
CPC .......... G01N 21/4795; G01N 21/532
USPC .......... 250/339.01–339.15, 340, 341.1–341.8
See application file for complete search history.

(56) References Cited

U.S. PATENT DOCUMENTS

| 5,345,081 A * | 9/1994 | Rogers | 250/338.1 |
| 6,037,591 A * | 3/2000 | Neri et al. | 250/341.1 |
| 6,585,341 B1 * | 7/2003 | Walker et al. | 347/14 |
| 6,873,680 B2 * | 3/2005 | Jones | 378/58 |
| 7,889,113 B2 * | 2/2011 | Cardiasmenos et al. | 342/22 |
| 2007/0257194 A1 * | 11/2007 | Mueller | 250/341.8 |

FOREIGN PATENT DOCUMENTS

WO    WO 2008112312 A1 *    9/2008 .............. A61B 5/00

OTHER PUBLICATIONS

T.C. Pearson, "Use of Near Infrared Transmittance to Automatically Detect Almonds with Concealed Damage," 1999, Adademic Press, Lebensm.-Wiss u-Tchnolo.,vol. 32, pp. 73-78.*

* cited by examiner

Primary Examiner — Kiho Kim
(74) Attorney, Agent, or Firm — Baker & Hostetler LLP

(57) ABSTRACT

Apparatus for inspecting an engineering material or food product comprising: a controller arranged to generate a time-variant drive signal; a source of Near Infra-Red (NIR) radiation, the source being operable by the controller to emit a repetitive time-varying beam thereby to illuminate an article; and a detector, the detector being configured to detect that portion of the source beam that has been transmitted through at least a portion of the article, and to generate an electrical signal that has a time variant modulation corresponding to the modulation of said portion of the source NIR beam, the controller being further configured to generate an output corresponding to a variation in the amplitude of the received NIR source beam.

19 Claims, 24 Drawing Sheets

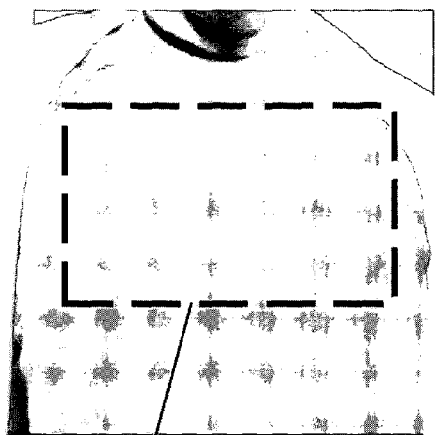
FIG. 16A  FIG. 16B
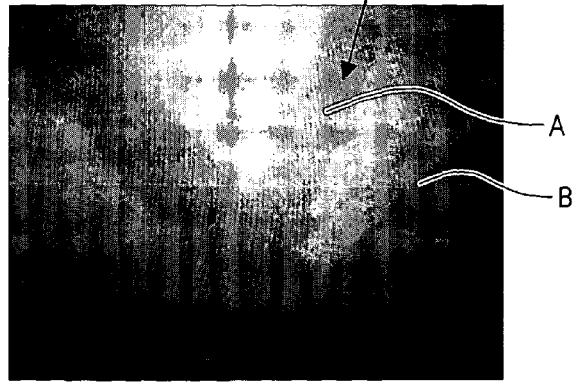
FIG. 16C

INSPECTION APPARATUS AND METHOD

CROSS-REFERENCE TO RELATED APPLICATIONS

This application is the National Stage of International Application No. PCT/GB2011/050643, filed Mar. 29, 2011, which claims the benefit of Great Britain Application No. 1005156.3, filed Mar. 29, 2010, Great Britain Application No. 1005157.1, filed Mar. 29, 2010, Great Britain Application No. 1007408.6, filed May 4, 2010, Great Britain Application No. 1010484.2, filed Jun. 22, 2010, Great Britain Application No. 1010650.8, filed Jun. 24, 2010, and Great Britain Application No. 1019544.4, filed Nov. 18, 2010, the disclosures of which are incorporated herein by reference in their entireties for any and all purposes.

FIELD OF THE INVENTION

Embodiments of the present invention relate to apparatus and a method for detecting concealed objects in an article. In particular but not exclusively embodiments of the invention relate to apparatus and a method which does not rely upon the necessity of imaging an internal structure. In particular, but not exclusively, the invention relates to apparatus and a method for detecting concealed objects and other inhomogeneities or defects inside the bulk of other objects.

In particular, some embodiments of the invention are of particular use in the field of Non Destructive Evaluation (NDE) of non-metallic engineering materials and the inspection of product in the food and pharmaceutical industries.

BACKGROUND

Increasing automation and demands for quality mean that inspection by human beings becomes impractical in some situations. In these circumstances, it is not always necessary to image the internal structure of an object being inspected in order to detect an internal fault or extraneous body or other concealed object.

Existing inspection tools such as x-ray imaging systems employ an inspection medium (in the case of x-ray systems the inspection medium is a beam of x-rays). The inspection medium may in some cases be referred to as an illuminating beam or an inspection beam.

Beams of x-rays have been used to investigate the internal structure and properties of a range of objects including engineering materials and food products. However, x-rays and other forms of ionising radiation present a range of health and safety issues. Apparatus employing x-ray radiation must be heavily shielded to ensure that personnel are not exposed to radiation.

Moreover, the size of an x-ray system is large and not suitable for many inspection situations. A further disadvantage of x-ray devices is their relatively high cost.

Another disadvantage of x-ray systems is many materials such as very thin layers of wood, plastics and thin polymer films are relatively radiolucent and very difficult to detect via x-rays.

A fundamental physical limitation of x-ray systems when used in an inline inspection application is that they cannot as readily image/detect an foreign body or contaminant which is less dense than the medium in which it is embedded as compared to being able to detect an object which is much denser than the article in which it is embedded Known inspection tools are typically imaging systems optimised for obtaining 2D or 3D spatially resolved images of a structure of a sample by exposing the sample to the inspection medium.

Image processing techniques are subsequently applied to the image to detect a presence of a foreign object, structural defect or other feature of interest. Such systems tend to be arranged to reduce or minimise scattering of the illuminating medium by the sample under inspection. This is in order to enhance a resolution of the imaging technique in some cases.

The present inventors have recognised that it is not necessary always to image an internal structure of a specimen to be inspected in order to conduct a meaningful inspection. Indeed, in some situations there may be an advantage in not imaging the internal structure. There may, in some situations, also be an advantage to enhancing the effects of internal scattering.

For example, it may be advantageous to employ an inspection technique where an object or feature to be detected interacts strongly with an inspection medium incident on the object or feature. The interaction may be characterised at least in part by distortion, scattering and/or absorption of the inspection medium.

The interaction may severely decrease the spatial resolution of an obtainable image of the object or feature. In many cases it may even render an image unobtainable However, if the principal aim of the inspection process is to determine whether or not the feature is present, and not to obtain a meaningful image of a structure of the object or feature, then such a technique may provide certain advantages.

For example, in the case of detection of an internal fault or extraneous object in a sample, it is desirable to be able to provide apparatus in which a detector can discriminate between a first condition in which a sample or portion of a sample not having an internal fault or extraneous object is present and a second condition in which a sample or portion thereof that does have such an internal fault or extraneous object is present. The greater the interaction of the inspection beam with the extraneous object, the greater the contrast at a detector between intensities of beams detected under the first and second conditions respectively.

Thus, it may be understood that a simple two-state detection system can be envisaged. The system may be provided in combination with a controller arranged to implement an algorithm arranged to provide a two state digital output, in accordance with Boolean principles. For example the controller may be arranged to output a high or low signal, or to illuminate a "red light" or "green light" depending on whether the first or second conditions described above are present.

STATEMENT OF THE INVENTION

In one aspect of the invention there is provided apparatus for detecting a concealed object in an article comprising: a source of Near Infra-Red (NIR) radiation operable to illuminate an article to be inspected; a detector, the detector being configured to detect that portion of the source beam incident on the detector that has been passed through at least a portion of the article; a collimator, the collimator having an entrance aperture, the collimator being arranged to collimate light passing through the entrance aperture that has passed through the article before it reaches the detector; and control means, the control means being arranged to detect by means of the detector an intensity of NIR illumination incident on the detector and to identify the presence of a concealed object in an article responsive to a variation in detected intensity across at least a portion of the article.

The concealed object may be an inclusion, other foreign body or a defect in the article. By concealed object is included a foreign body that is located underneath the article under inspection and thereby concealed by it as well as an object that is contained within the article. Some embodiments are arranged to detect inclusions, other foreign bodies or defects that are visible at a surface of an article such as an upper surface and which are not necessarily concealed.

It is to be understood that embodiments of the present invention are not necessarily directed to apparatus and a method for imaging concealed objects. Rather, embodiments of the invention are directed to identifying whether or not a concealed object is present in an article based on scattering of NIR radiation by the object. Thus embodiments of the invention are distinguished over the prior art in that the prior art teaches to detect concealed objects by transmitting radiation through an article in order to form an image of the concealed object rather than to detect the object without forming an image of the object.

Embodiments of the invention are particularly suited to imaging of concealed articles in a turbid medium such as a cheese, a fruit or the like. Unlike X-ray inspection techniques embodiments of the invention are able to detect the presence or absence of materials having a low scattering cross-section for X-ray radiation such as paper, fruit pips and fruit stones and the like.

Known inspection techniques employing NIR radiation are directed to overcoming a perceived problem of scattering of NIR radiation by a turbid medium. Conversely, embodiments of the present invention are directed to using scattering to our advantage in order to enhance detection of foreign objects via the "shadowing effect" of the articles on radiation incident on the detector. This shadowing effect is greatly enhanced in the presence of the collimator enabling detection of concealed objects reliably and cost effectively.

The detector may comprise an elongate detector.

The detector may comprise a plurality of detector elements such as a plurality of photodiodes. In some arrangements the detector comprises a position sensitive detector in addition or instead.

In some arrangements the detector comprises a 2D detector. Optionally the 2D detector comprises an array of photo-detector elements such as photodiodes or a position sensitive area detector.

Advantageously the collimator comprises a slit-type collimator having an elongate entrance aperture in the form of a slit, the elongate entrance aperture being oriented substantially parallel to the elongate detector.

The use of a slit-type collimator has the advantage that an acceptance angle of the detector with respect to radiation travelling parallel to a plane normal to a longitudinal axis of the detector may be limited. However, the acceptance angle with respect to radiation travelling in a plane that includes the longitudinal axis of the detector may be larger, in some arrangements by a factor of from around 5 to around 10.

The length of the slit may be selected to allow light scattered by the sample across a full lateral extent of the sample of interest to be accepted by the collimator for detection by the detector.

The limitation in angular acceptance angle of the detector with respect to radiation travelling parallel to a plane normal to a longitudinal axis of the detector has the advantage that a position of a concealed object such as an inclusion, defect or foreign body may be determined more precisely. For example, if an article is passed through the apparatus between the source and the detector along a first axis of the article (e.g. a y-axis) the location of the concealed object may be determined with respect to the y-axis. In some arrangements with certain types of concealed object, determination of the location of the concealed object with respect to a second axis (e.g. an x-axis) normal to the first axis but parallel to the longitudinal axis of the detector may be non-trivial or substantially impossible. However this is not a problem in some embodiments of the invention where it is sufficient to determine a location of the concealed object along the y-axis.

The collimator may comprise a plurality of substantially parallel pipe elements, the collimator being arranged to allow light passing through the entrance aperture to be incident on the detector only if the light is travelling along a direction substantially parallel to a longitudinal axis of the pipe elements.

The apparatus may be arranged to expose a sample to radiation propagating at a plurality of angles with respect to the sample.

The source may comprise a fan-type source arranged to emit light of relatively large divergence.

The fan source is advantageously arranged to emit light of relatively large divergence in a first plane and of relatively low divergence in a second plane normal to the first plane, the first plane being aligned with the entrance aperture of the collimator.

By fan-type source is included a source having a relatively large divergence with respect to light travelling in a first plane and a relatively low divergence with respect to light travelling in a second plane normal to the first plane.

Alternatively the source may be arranged to emit light of relatively large divergence in first and second orthogonal planes.

The apparatus may be arranged diffusely to illuminate the sample.

The apparatus may comprise a diffuser arranged to scatter light from the source onto the sample thereby to illuminate diffusely the sample.

The source may comprise a plurality of light emitting elements at different respective spatial locations. The spatial locations may be substantially co-linear.

Advantageously the detector is operable to output a signal responsive to an intensity of radiation incident thereon at each of a plurality of different spatial locations.

The detector may comprise a plurality of photodetector elements, the detector being operable to output respective values of intensity of NIR radiation incident upon the elements.

Alternatively or in addition the detector may comprise a position sensitive detector.

Advantageously the detector is arranged to detect an amount of radiation falling thereon from each of the light emitting elements at spatially separate locations corresponding substantially to a substantially direct path of NIR radiation from each detector through the article.

Optionally the detector comprises a plurality of photodetectors. The photodetectors may be provided in a substantially linear array. The linear array of photodetectors may be substantially parallel to a linear array of light emitting elements.

By linear array is included a single file line of detectors that are co-linear with a straight line or a curved line.

By linear array is also included an array that is linear for the purpose of the application, i.e. an array in which two or more rows of detector elements are provided but wherein a length of the array is much larger than a width of the array, for example by a factor of at least 5. In some alternative arrangements by linear array is meant an array in which a length of the array is larger than the width by a factor of at least around 10.

In some arrangements respective photodetectors may have an optic axis substantially coincident with an optic axis of a corresponding source element.

The apparatus may be operable to illuminate at least one but not all of the source elements and to detect by means of the detector light incident thereon from the at least one illuminated source element at a plurality of different spatial locations.

This feature has the advantage that a shadow cast by the at least one source element on the detector may be detected thereby to enhance detection of a concealed object.

The apparatus may be operable to subsequently illuminate at least a different one but not all of the source elements and to detect by means of the detector light incident thereon from the at least one illuminated source element at a plurality of different spatial locations.

Alternatively or in addition the apparatus may be operable to illuminate each source element in turn and to detect by means of the detector light incident thereon from each respective source element in turn at a plurality of different spatial locations.

This feature has the advantage that the article may be illuminated across at least a portion thereof in a sequential, 'scanned' manner and a change in a shadow cast on the detector monitored as a function of position of the illuminating beam thereby to enhance detection of a concealed article.

In some embodiments the apparatus may be arranged to illuminate the source elements in pairs or other numbers of source elements in order to detect a concealed object responsive to a pattern of a shadow falling on the detector and changes in the shadow responsive to changes in the identity of the source element or source elements illuminated at a given moment in time.

The apparatus may be operable to illuminate each source element in turn and to detect by means of the detector light incident thereon from each respective source element in turn at a position of the detector corresponding substantially to a substantially direct path of NIR radiation from each detector through the article.

The substantially direct path may be the path of least distance from the source element to the detector.

Advantageously the source comprises one selected from amongst a linear (1D) array of light emitting elements and a 2D array of light emitting elements.

Advantageously the detector comprises one selected from amongst a linear (1D) array of photodetector elements and a 2D array of photodetector elements.

Optionally a distance between the object under inspection and a detector plane being the plane at which illumination is detected by the detector is adjustable.

The apparatus may be operable to irradiate the sample with polarised radiation, the apparatus being configured to detect a change in polarisation of the radiation by the sample.

The apparatus may be operable to measure a first intensity of radiation detected by the detector with a polarising filter between the article and detector and a second intensity of radiation detected by the detector in the absence of the polarising filter.

Advantageously the polarising filter is arranged to block light having the same polarisation as the incident light.

That is, the polarising filter may be in a 'crossed' condition with respect to the incident polarised illumination. Alternatively in some arrangements a 'parallel' polarisation condition of the polarising filter may be employed.

The apparatus may be configured to detect a concealed object responsive to a difference between the first and second intensities.

It is to be understood that this feature has the advantage that a relatively simple subtraction technique may be employed in order to extract a value of intensity of light that is unscattered by the sample. This is because the first intensity of light detected by the detector corresponds to the intensity of scattered light (being light having its polarisation changed by scattering) and the second intensity corresponds to the intensity of both scattered and unscattered light.

Advantageously the apparatus may be arranged to direct the radiation to pass from the source to the detector through a medium being a medium arranged to convey the sample past the detector.

The apparatus may be arranged to direct the radiation to pass through a conveyor as it passes from the source to the detector.

Thus radiation transmitted between the source and detector through the article may be required to pass through a conveyor such as a conveyor belt or the like. It is to be understood that conveyor belts may be readily formed from a material that is transparent to NIR radiation (such as a rubber, a plastics material and/or an elastomer). In some arrangements the detector is provided below a conveyor belt that is opaque to visible radiation but translucent or transparent to NIR radiation in an inline inspection apparatus installed at a production line.

Advantageously a signal from the detector corresponding to the intensity of NIR incident thereon is subject to logarithmic amplification whereby an amount of amplification of a signal decreases as a function of signal amplitude according to a logarithmic relationship.

Thus some embodiments of the invention may employ a logarithmic amplifier in the detector circuit. This has the feature that relatively small signals are amplified to a greater extent than larger signals. Thus recalibration of the apparatus may not be necessary in some arrangements. Some such embodiments may also be more adaptive to variations in thickness and density of an article under inspection.

The apparatus may comprise a beam splitter and at least two detectors, the beam splitter being arranged to split the beam transmitted through the sample and to direct respective split portions of the beam to a respective one of the at least two detectors.

This feature has the advantage that two detectors may be employed to detect radiation without introducing parallax between the regions of the article from which the detectors detect radiation at a given moment in time.

At least one of the two detectors may be configured to detect visible radiation.

Advantageously said one of the at least two detectors is configured to form an image of the article.

Thus one of the detectors may be arranged to form an image of the article under inspection. The image may be used in order to identify an article under inspection, and/or to identify where a concealed object detected by the other detector is located.

Optionally one of the detectors is arranged to detect NIR radiation of a first frequency and not a second frequency and another of the detectors is arranged to detect NIR radiation of the second frequency and not the first frequency.

This feature has the advantage that spectral inspection of an article may be performed thereby to enable identification of a chemical composition of the article or an object concealed by the article.

Advantageously at least one of the two detectors comprises a spectrometer arranged to provide a signal responsive to an intensity of radiation of a given frequency as a function of frequency.

The control means may be arranged to generate a time-variant drive signal to drive the source of Near Infra-Red (NIR) radiation thereby to emit a source beam having a repetitive time-varying intensity, whereby the control means may determine a size of a component of the intensity of radiation detected by the detector corresponding to the source.

Advantageously the controller is configured to perform an autocorrelation or other lock-in function between the drive signal and the detected intensity of radiation thereby to enable the apparatus to detect a concealed object.

The controller may be configured to apply a bandpass filter to a signal corresponding to the intensity of detected radiation thereby to enable the apparatus to detect a concealed object.

In some arrangements the apparatus may be arranged to perform one or more of a heterodyning or a homodyning function in respect of the intensity of detected radiation in order to enable the apparatus to detect a concealed object.

The apparatus may be arranged to implement a negative feedback process wherein the intensity of NIR radiation generated by the source is responsive to the intensity of radiation from the source detected by the apparatus.

Thus an auto calibration process may be implemented which may be especially useful in circumstances where a thickness or other feature of an article is found to vary within an article or between articles, for example where an article has a continuously changing thickness.

In some embodiments a distance between the object under inspection and the detector plane, being the plane at which illumination is detected by the one or more detectors, may be adjustable depending on a sample under inspection and available illumination. Other factors may also affect the choice of distance between object and detector plane.

The source may be configured to generate a beam of NIR radiation having an intensity that is modulated in a periodic manner, wherein the intensity of the modulated beam is arranged to vary as a function of time.

That is, the amplitude of modulation of the beam may itself be modulated such that the modulated beam has a first intensity over one or more modulation cycles and a second intensity over one or more other modulation cycles.

Optionally the source is configured to generate a beam having an intensity that is modulated at a first amplitude and subsequently at a second amplitude, the apparatus being configured to detect a concealed object by reference to radiation from the source that is modulated at the first or second amplitude responsive to an intensity of the signal generated by the source that is detected by the detector.

Thus, in the event that an article under inspection transmits a relatively small amount of radiation the apparatus may be configured to employ the portion of the detected signal corresponding to the source beam of higher intensity to detect a concealed object whilst in the event that an article that transmits a relatively large amount of radiation is under inspection the apparatus may be configured to employ the portion of the detected beam source beam that is of lower intensity Advantageously, in embodiments in which the source is arranged to be modulated at a modulation frequency, the apparatus comprises a unit for performing lock-in demodulation of a plurality of input signals, each signal corresponding to an intensity of radiation falling on each one of a corresponding plurality of locations of the detector comprising: an input portion arranged to receive the plurality of input signal; a lock-in demodulation portion arranged to demodulate the plurality of input signals; and an output portion arranged to provide a plurality of output signals corresponding to each of the demodulated input signals.

The lock-in demodulation portion may comprise a parallel lock-in demodulation portion.

The parallel lock-in demodulation portion may be arranged to perform lock-in demodulation of a plurality of input signals substantially simultaneously.

Alternatively or in addition the lock-in demodulation portion may comprise a serial lock-in demodulation portion.

The serial lock-in demodulation portion may be arranged to perform lock-in demodulation of a plurality of input signals substantially sequentially.

The input portion may comprise a plurality of input signal lines each line being arranged to receive at least one of the plurality of input signals.

Optionally the number of input signal lines corresponds to the number of input signals.

The number of input signal lines may be substantially equal to the number of input signals.

The output portion may comprises a plurality of output signal lines each line being arranged to provide at least one of the plurality of output signals.

The number of output signal lines may correspond to the number of output signals.

Optionally the number of output signal lines is substantially equal to the number of output signals.

The output portion may comprise a multiplexer arranged to provide a serial output of the output signals.

In a further aspect of the invention there is provided a method of detecting a concealed object in an article comprising: illuminating an article to be inspected with Near Infra-Red (NIR) radiation; detecting by means of a detector that portion of the source beam incident that has been passed through at least a portion of the article; collimating by means of a collimator light that has passed through the article before it reaches the detector; and identifying by means of control means the presence of a concealed object in an article responsive to a variation in detected intensity across at least a portion of the article.

The method may comprise passing the radiation through a collimating means in the form of a slit-type collimator.

Advantageously the article or object comprises a container in which a material is contained, the method comprising passing NIR radiation of a prescribed frequency or range of frequencies through the container and through the material and detecting a chemical identity of the material responsive to absorption of the radiation by the material.

The prescribed frequency or range of frequencies may correspond to a frequency or range of frequencies at which the material scatters a relatively large amount or radiation and the container scatters a relatively low amount of radiation.

Advantageously the prescribed frequency or range of frequencies corresponds to a frequency or range of frequencies at which the material absorbs a relatively large amount or radiation and the container absorbs a relatively low amount of radiation.

The method may comprise the step of subtracting from the detected signal a signal corresponding to a signal that would be detected from the container alone.

Optionally the material comprises one selected from amongst a gel, a cream, a powder, an emulsion, a liquid and a solid.

The method may comprise the step of irradiating the article with NIR radiation of a plurality of frequencies; and detecting an intensity of NIR radiation transmitted through the sample as a function of frequency.

Thus in some embodiments a chemical absorption spectrum may be obtained, in some embodiments the spectrum being a substantially continuous spectrum as a function of frequency. If the identity of the material from which the container is formed is known, its composition spectrum can be then subtracted to permit chemical identification of the contents of the container alone.

Furthermore, if an absorption spectrum is obtained from the container alone, for example by transmission of NIR radiation through the container above the interior level of the contents and then at a location where the beam penetrates through the material within the container in addition then in some arrangements two separate spectra may be obtained, optionally in a single measurement using a 1D or 2D detector. Again, a subtraction of the spectra from the container only from that of the container and contents may enable a spectrum from the contents only to be obtained.

It is to be understood that for the present purposes by 1D detector is meant a substantially linear detector, ie an elongate detector such as a line of photodiodes. Reference to a linear detector includes reference to a linear detector describing a curve, i.e. detector elements of the detector do not lie in a straight line, as well as a detector in which the detector elements do lie in a substantially straight line. A point detector such as a single photodiode would be referred to as a 0D (zero dimensional) detector.

Other arrangements are also useful.

In one aspect of the present invention there is provided apparatus for inspecting an article, the apparatus comprising: a source of Near Infra-Red (NIR) radiation arranged to direct NIR radiation through at least a portion of the article; and a detector, the detector being configured to detect radiation which either passes through, or is absorbed or is scattered by the article, the apparatus being configured to provide an output responsive to a variation in intensity of NIR radiation from the source that is incident upon the detector.

For the avoidance of doubt it is stated that features associated with any aspect of the invention described herein are described as being suitable for use with any other aspect described herein.

The apparatus may be operable to control the source to emit a beam of NIR radiation that varies in intensity according to a drive signal thereby to allow the apparatus to distinguish between detected NIR radiation emitted by the source and detected radiation not emitted by the source.

The beam may be arranged to vary in intensity in a periodic manner.

The beam may be arranged to vary in intensity in a periodic manner corresponding to a variation in amplitude of the drive signal.

The apparatus may be arranged to discriminate between NIR radiation emitted by the source and radiation not emitted by the source by means of a reference signal having a frequency that corresponds to the frequency of the drive signal.

The article may comprise an engineering material or food product.

In another aspect of the invention there is provided apparatus for inspecting an article comprising: a controller arranged to generate a time-variant drive signal; a source of Near Infra-Red (NIR) radiation, the source being operable by the controller to emit a beam of repetitive time-varying intensity corresponding to the time variation of the drive signal thereby to illuminate the article; and a detector, the detector being configured to detect that portion of the source beam that has been transmitted through at least a portion of the article, and to generate an electrical signal corresponding to the intensity of radiation from the source beam incident thereon.

Thus the apparatus is arranged to distinguish between background NIR or other detected radiation and radiation from the source.

The article may comprise an engineering material, a food material or a pharmaceutical material. Other materials are also useful.

The controller may be arranged to provide an output corresponding to an intensity of NIR radiation from the source that has been detected by the detector.

The output may be in the form of a DC potential.

Apparatus according to embodiments of the invention has the advantage that it is capable of detecting the presence of inclusions and other faults within an article without exposing said article to ionizing radiation. Consequently, apparatus according to embodiments of the invention does not require the necessary ionizing radiation shields and other precautions associated with prior art techniques such as X-ray inspection to prevent exposure of operatives to harmful radiation.

The apparatus may be arranged to discriminate between NIR radiation emitted by the source that is detected by the detector and radiation not emitted by the source that is detected by the detector by reference to a reference signal having a frequency that corresponds to the frequency of the drive signal.

The reference signal and drive signal may have the same frequency as one another and the apparatus may be configured to implement a lock-in or homodyning function between the reference signal and the detector signal detected by the detector.

Alternatively or in addition the reference signal may be a periodic reference signal having a frequency different from the drive signal. The apparatus may be arranged to implement a heterodyning function between the reference signal and the drive signal.

Alternatively the device could employ a suitably tuned receiver circuit which is independent of the source and the source modulation generator that generates the drive signal.

The tuned receiver may be arranged to implement a filter having a pass-band of a frequency width appropriate to the particular application.

The apparatus may be configured to implement an auto-correlation function between the reference signal and the detector signal thereby to generate the DC signal value.

Optionally the beam of NIR radiation corresponds to NIR radiation having a wavelength in the range 700 to 1100 nm. And preferentially, though not exclusively, three specific wavelengths: 850 nm, 980 nm and 1064 nm This range of wavelength corresponds to a range in which many materials are relatively transparent to electromagnetic radiation as compared to the range of wavelengths which comprise the visible part of the electromagnetic spectrum. Thus, this range of wavelength corresponds to the NIR range range in which a sufficient amount of radiation may be transmitted through a sample to enable inspection of an internal structure of the sample to be made in a reasonable length of time.

This range of wavelength, (with the exception of those wavelengths approximately between 970 nm and 1000 nm) also corresponds to wavelengths to which water is relatively transparent. Thus, imaging of the internal structure of water-containing materials such as food products is possible using NIR radiation.

The apparatus may be operable to move the detector with respect to the article to be inspected.

Alternatively or in addition, the apparatus may be operable to move the article to be inspected with respect to the detector.

In some embodiments of the invention, the relative position of the source with respect to the detector remains substantially unchanged whether the detector is moved with respect to the article or the article is moved with respect to the detector.

In an industrial application, such as the bulk inspection of foodstuffs, the detector can be behind or underneath a sometimes, visibly-opaque conveyor belt in which case the NIR signal passes through both the article and the conveyor belt.

The detector may comprise an array of photo-detector elements.

This feature has the advantage that parallel collection of data may be performed. In other words, detection of NIR radiation from the source that has interacted with the article to be inspected may be made at a plurality of spatially separate locations at substantially the same time. This has the advantage that it enables data to be collected from a plurality of spatially separate locations more quickly than in the case of serial collection of data. By serial collection of data is meant that data is collected from one spatial location, and subsequently from a second spatial location by moving the detector with respect to the sample or vice-versa.

The array may be a linear array. Alternatively the array may be a planar array.

A planar array has the advantage that data may be obtained over a two dimensional area without a requirement to move the detector or the article under inspection.

The apparatus may be configured to operate in a transmission mode whereby the detector is arranged to detect a beam of NIR radiation transmitted through the article to be inspected from one side of the article to the other, the detector being provided on a side of the sample substantially opposite a side wherein the source is provided.

Alternatively or in addition the apparatus may be configured to operate in a reflection mode whereby the detector is arranged to detect a beam of NIR radiation reflected by the article to be inspected. The detector may be provided on substantially the same side of the article as the source.

Reference to a reflection mode is to be understood to include reference to a mode in which reflection of the NIR radiation from the source occurs for example from a surface of an article such as an outer surface and/or an inner volume of the article such as an interface between a matrix and an embedded particle, the reflected radiation being detected. The surface of the article may be an outer surface, for example an outer surface that the NIR radiation encounters after having passed through at least a portion of the article. It will be understood by those skilled in the art that the reflection mode of operation therefore includes detection of NIR radiation that has been transmitted through at least a portion of the article under inspection, and is not limited only to detection of NIR radiation reflected from an outer surface of the article.

Moreover using modulated NIR for depth resolution and imaging of a plane underneath the surface of an article could also be accomplished in reflection mode via a method similar to established Confocal microscopy techniques—but unlike conventional Confocal microscopy techniques does not rely upon fluorescence In a variation of the reflection mode of operation, in some embodiments of the invention one or more reflective elements are provided to reflect NIR radiation transmitted through the specimen back through the specimen to a detector provided on substantially the same side of the specimen as the source.

For example, a reflective element such as a metallic surface, for example a sheet of metallic material such as a foil may be arranged to reflect radiation back through the sample. The reflective element may be provided by the article under inspection, such as a portion of packaging of the object such as a seal, a lid or the like.

For example, the sample may comprise a reflector member and a portion of interest such as a pharmaceutical, a foodstuff or any other sample of interest. The pharmaceutical or foodstuff may be in the form of tablets. The tablets may be contained within a packaging having a layer of a reflective material providing the reflector member.

Thus, the reflector member may be provided by a foil of packaging in which the foodstuff or pharmaceutical is stored. For example blister-packs and other packaging such as food packaging, beverage packaging and the like in which a container such as a container formed from a plastics material is provided with a removable seal such as a metallic foil seal. It is to be understood that the container may be inspected with the source of radiation arranged to transmit light through the sample, the detector being arranged to detect light scattered by the foil back through the container.

The inspection of articles which comprise the reflector member have the advantage that inspection of the sample may take place without the further constraint that the apparatus must provide a reflector member. This is particularly advantageous in production line environments where e.g. conveyors such as conveyor belts are employed. The apparatus may be mounted beneath a conveyor belt where the conveyor belt is arranged to allow transmission of NIR radiation therethrough.

Other arrangements are also useful.

Alternatively or in addition the reflective element may be part of the apparatus itself. Thus for example a conveyor such as a conveyor belt may be arranged to reflect NIR radiation emitted by the source after it has passed through the sample back towards the detector.

In some embodiments the source of radiation and the detector may be positioned on the same side of the sample.

Optionally, the apparatus may be responsive to a polarisation of light in the NIR range.

Preferably, the apparatus is responsive to a polarisation of NIR radiation reflected by a portion of a sample such as a hidden and/or submerged dielectric object such as glass. Such reflected radiation may maintain its polarisation state and be detectable by an analyser and indicate the presence of a reflecting dielectric material such as glass or plastics The apparatus may be configurable to operate in either a reflection mode or a transmission mode. The apparatus may be configurable to operate in a reflection mode and a transmission mode simultaneously.

The source may be configured to emit NIR radiation of a plurality of wavelengths.

The detector may be configured to detect NIR radiation of a plurality of wavelengths.

A plurality of detectors may be provided, each detector being configured to detect NIR radiation of a different respective wavelength or range of wavelengths.

In some arrangements a respective filter may be provided between each detector and the sample whereby each detector may be configured to detect NIR radiation of a different respective wavelength or range of wavelengths.

This feature has the advantage that the apparatus may be used to measure an amount of radiation absorbed or scattered by a sample as a function of wavelength of the radiation substantially simultaneously. It is to be understood that in some materials an amount of scattering of the radiation is a function of wavelength of the radiation. Thus, in some arrangements features of an internal structure of an article may be elucidated by obtaining scattering data at different respective wavelengths.

Optionally, adjacent detectors may be sensitive to the same wavelength but be arranged to respond to a different time variant modulation frequency. In some arrangements control apparatus associated with the detectors may be arranged to respond to different time-variant modulation frequencies; for example in some arrangements a tuner associated with a detector may be tuned to a different frequency from that of an adjacent detector.

Optionally, the same detectors may be subjected to rapidly changing variations in intensity of radiation of the same wavelength but different intensities, one intensity being calibrated against the least thick and least attenuating part of an article and one intensity being calibrated against the most thick and most attenuating part of an article so as to provide an interlaced output which detects inclusions and embedded objects with greater discrimination. Thus the radiation of lower intensity is arranged to be of an intensity suitable for providing useful data from the least thick and/or least attenuating part of the article and the radiation of highest intensity arranged to be of an intensity suitable for providing useful data from the most thick and/or most attenuating part.

In some arrangements a beam of NIR radiation is provided having a modulated signal intensity, which intensity is itself modulated between a relatively high intensity and a relatively low intensity from a single beam as also described above.

This feature has the advantage of increasing a likelihood that a useful signal will be obtained from a detector arranged to detect radiation transmitted through an article under inspection.

As also noted above, apparatus according to embodiments of the present invention may be configured to compare data in respect of the intensity of radiation transmitted by the sample and detected by the detector and to determine whether to use data recorded using modulated radiation of the lower intensity, the higher intensity or both.

Thus, for example if the article under inspection (or portion thereof) is a relatively highly transmissive article or portion thereof, the apparatus may be configured to employ data in respect of the radiation incident on the article of lower intensity. If on the other hand the article transmits only a relatively small amount of radiation incident thereon the apparatus may be configured to employ data in respect of the radiation of higher intensity incident on the article.

As noted above a signal recovery technique may be employed to detect the modulated beam, and be arranged to extract the portion of higher intensity, lower intensity or both.

The detector may comprise a tunable optical filter.

This has the advantage that the same detector may be used to measure the amount of radiation incident upon the detector at each of a plurality of wavelengths or range of wavelengths. That is, by performing a plurality of measurements of an amount of NIR radiation detected by the detector, and changing the characteristics of the filter between measurements (thereby to change the wavelength of NIR radiation passed by the filter), the relative amounts of attenuation of a signal by the sample as a function of wavelength may be determined.

At least one of said wavelengths may correspond to a characteristic absorption wavelength of an article or portion thereof.

The source may be or comprise a laser source. Laser sources have the advantage that collimation of a beam of radiation from the source is not required. In some embodiments of the invention a laser beam is projected across the sample thereby to obtain an image of a cross-sectional area of the sample, in a similar manner to laser barcode scanning technology.

In other embodiments of the invention, the source may be an array of Light Emitting Diodes (LEDs) that emit radiation in the NIR band of the electromagnetic spectrum. Other sources are also useful.

At least one of the sources may comprise a fibre optic cable which admits NIR radiation of the wavelengths within the NIR band described above.

The apparatus may be arranged to expose a sample to radiation at a plurality of angles with respect to the sample.

Thus some embodiments employ a fan-type source as described elsewhere herein.

In some embodiments the apparatus is arranged to provide diffuse illumination of a sample. The apparatus may comprise a diffuser arranged to scatter light from the source onto the sample. Alternatively or in addition a plurality of radiation sources may be provided at different respective spatial locations. The sources may for example be arranged in an array, such as a one or two-dimensional array. Thus, illumination from different respective sources will have different respective angles of incidence on the sample under inspection.

It is to be understood that some embodiments of the invention seek to increase a detectability of a presence of an object or feature by increasing an amount of contrast between detected signals in the presence and absence of the object or feature.

For example, some embodiments seek to increase contrast by providing inspection beams at a plurality of angles of incidence to the sample as described above.

This feature may be particularly advantageous when highly scattering media are employed such as powders, particulates, colloidal suspensions, solid emulsions and other media. The use of diffuse or diffused illumination of a sample has been found to provide a surprising increase in an amount of contrast between a defect or feature of interest and a surrounding medium.

It is to be understood that prior art techniques for detecting concealed objects rely on reducing scattering or providing techniques for reducing the effects of scattering, rather than by seeking to increase an amount of scattering. Known techniques typically rely on forming images of a structure of an article by absorption contrast imaging and detecting the presence of a concealed object by image analysis.

In addition or instead, in some embodiments contrast between signals detected in the presence or absence of a scatting object of interest may be increased by increasing a distance between the sample and detector. This has the effect that a size of a 'shadow' cast on a detection plane by the feature or object of interest may be increased.

Thus the detector may be provided sufficiently far from an exit plane of radiation from the sample to provide a required contrast level.

It is to be understood that a trade off between intensity and contrast may be required to be made in order to obtain an optimum signal.

It may also be useful for a negative-feedback process to be implemented to control the intensity of the NIR illumination in order to maximise the detectivity of an embedded object in an article. Thus, the apparatus may be arranged whereby the intensity of NIR illumination generated by the source is responsive to the intensity of NIR radiation detected by the apparatus. Thus an auto calibration process may be implemented which is especially useful in circumstances where a thickness or other feature of an article is found to vary within an article or between articles, for example where an article has a continuously changing thickness.

In some embodiments a distance between the object under inspection and the detector plane, being the plane at which illumination is detected by the one or more detectors, may be adjustable depending on a sample under inspection and available illumination. Other factors may also affect the choice of distance between object and detector plane.

In some embodiments it is desirable to increase a sharpness of a spatial distribution of illumination scattered by an object under inspection. In other words, it is desirable to decrease an amount of illumination incident upon a given detector that has experienced multiple scattering events by a sample.

In some embodiments it is desirable to decrease an amount of illumination incident on a sample that has experienced any scattering interaction with a sample.

In the case of a beam passing through a volume of the sample, in some embodiments it is desirable that only a portion of the beam being a portion that has passed substantially directly through the sample (and has not been scattered by the sample) is incident on a detector.

Thus, a collimator may be provided between the detector and the sample in order to restrict an angular range of illumination incident on the detector.

In addition or instead, the apparatus may be arranged to provide illuminating radiation in the form of a substantially parallel beam.

The beam of illuminating radiation (whether a parallel beam or a fan-type beam or other non-parallel and/or diffuse beam) may be arranged to be a beam of plane-polarised radiation. Thus, the beam may be arranged to pass through a polarising element before being incident on the sample, or be generated by a polarised light source.

The beam may then be arranged to pass through a polarising element (which may be referred to as an analyser) after exiting the sample and before entering a detector. The analyser may be oriented substantially parallel to the plane of polarisation of light incident on the article, in a 'parallel polarisation' arrangement. Alternatively a 'crossed polarisation' arrangement may be employed where the planes are substantially orthogonal.

It is to be understood that as the beam passes through the sample the polarisation state of the illumination may decay in certain portions of the sample due to scattering. Scattered illumination will therefore have a reduced chance of passing through the second polarising filter thereby increasing an amount of contrast of a signal at the detector in the presence or absence of a scattering feature such as a defect, inclusion, foreign body or other feature as described above.

In some embodiments a source in the form of a linear array of source elements (which may also be referred to loosely as sources) and a linear array of corresponding matched receivers are provided at opposite ends of an optical axis. A 2-D area detector may alternatively be provided, optionally with a 2D array of source elements. The 2D detector may be a position sensitive detector (PSD) or an array of photodiode or other receivers.

The array of source elements and the array of detectors may be a 'matched' array in that an optical axis of each source element of the array of source elements may be substantially coincident with an optical axis of each detector of the array of detectors. Other arrangements are also useful. Each source element and corresponding detector sharing an optical axis may be described as a matched pair.

It is to be understood that sequentially switching on each matched pair (i.e. one source element and one detector) in isolation will further reduce the effects of scattering compared with embodiments in which more than one source element is switched on during a process of detection. This is because illumination detected by a detector substantially directly opposite a given source element when only that source element is switched on will tend to be illumination that has passed through the sample in a substantially direct line of sight from the source element to detector with little or no scattering (depending on the arrangement of the collimator). If more than one illumination source element is switched on, illumination from that source element that is scattered by the sample may be scattered into a detector other than the corresponding matched detector in line of sight view of that source element.

It is to be understood that a matched source element and detector pair need not have optical axes that are precisely coincident in order to obtain the benefit described above.

In some arrangements in which it is desirable to exploit the effects of scattering of NIR radiation by a sample, one or more sources of the array of source elements (which may be a 1D or 2D array as noted above) are illuminated and signals provided by one or more detectors displaced in a lateral direction with respect to the optical axis of the source elements (i.e. a direction normal to the optical axis) are employed to detect illumination from the source elements.

This feature has the advantage that a shadowing effect of an inclusion or other foreign body on radiation illuminating the article under inspection may be enhanced. That is, a 'shadow' falling on the detector array due to an inclusion of other foreign body in or on an article under inspection may be detected by the array.

In some arrangements one or more of the source elements (but not all) are illuminated simultaneously and an intensity of radiation incident on all or one or more of the detectors measured, before illuminating simultaneously one or more other of the source elements and detecting an intensity of radiation incident on all or one or more of the detectors.

In some arrangements two or more source elements are illuminated simultaneously that are sufficiently far apart that an amount of light from one source element that is scattered to a detector substantially opposite the other source element is sufficiently small not to reduce the contrast at the detector between light from said other source element and light not from said other source element significantly. By not significantly is meant that the contrast reduction is less than 50%, optionally less than 20%, optionally less than 10%.

In some alternative arrangements all of the source elements are illuminated simultaneously.

In some arrangements one source element is illuminated at a time and an intensity of light incident on each detector is measured whilst each of a plurality of the source elements are illuminated in turn in order to enhance an amount of contrast due to scattering. In some arrangements each of the source elements are illuminated in turn.

As discussed above, in some embodiments of the invention apparatus is provided that is arranged to implement a small signal recovery technique by modulating the intensity of the source beam and detecting a corresponding modulation in intensity of illumination detected by the detector.

In one aspect of the present invention there is provided apparatus for inspecting an engineering material or food product comprising: a controller arranged to generate a time-variant drive signal; a source of Near Infra-Red (NIR) radiation, the source being operable by the controller to emit a beam of time-varying intensity corresponding to the time-variation of the drive signal thereby to illuminate an article; and a detector, the detector being configured to detect that portion of the source beam that has been transmitted through at least a portion of the article, and to generate an electrical signal corresponding to the intensity of the portion of the source NIR beam detected, the controller being further configured to generate an output corresponding to a variation in the intensity or amplitude of the received NIR source beam.

In one aspect of the present invention there is provided a unit for performing lock-in demodulation of a plurality of input signals comprising: an input portion arranged to receive a plurality of input signals; a lock-in demodulation portion arranged to demodulate the plurality of input signals; and an output portion arranged to provide a plurality of output signals corresponding to each of the demodulated input signals.

The lock-in demodulation portion may comprise a parallel lock-in demodulation portion.

Preferably the parallel lock-in demodulation portion is arranged to perform lock-in demodulation of a plurality of input signals substantially simultaneously.

Alternatively the lock-in demodulation portion may comprise a serial lock-in demodulation portion.

Preferably the serial lock-in demodulation portion may be arranged to perform lock-in demodulation of a plurality of input signals substantially sequentially.

The input portion may comprise a plurality of input signal lines each line being arranged to receive at least one of the plurality of input signals.

The output portion may comprise a plurality of output signal lines each line being arranged to provide at least one of the plurality of output signals.

The number of input signal lines may correspond to the number of input signals.

The number of output signal lines may correspond to the number of output signals.

In addition to or instead of a plurality of output signal lines the unit may comprise a multiplexer arranged to provide a serial output of the output signals.

The unit may be arranged to receive an input from a plurality of transducers. Optionally the transducers may be at least one selected from amongst audio transducers such as microphones; optical detectors such as photodiodes; electromagnetic detectors; electrostatic detectors; and strain gauges.

Thus it is to be understood that some embodiments of the invention are arranged to receive a multiple channel parallel input from multiple detectors/transducers and to perform a parallel lock-in process. The detectors/transducers may be in the form of a linear array.

In another aspect of the invention there is provided a method of performing lock-in demodulation of a plurality of input signals comprising: receiving at an input portion a plurality of input signals; performing a lock-in demodulation process thereby to demodulate the plurality of input signals; and outputting at an output a plurality of output signals corresponding to each of the demodulated input signals.

In a further aspect of the present invention there is provided a unit for performing parallel lock-in demodulation comprising: an input portion arranged to receive a plurality of input signals; a parallel lock-in demodulation portion arranged to demodulate the plurality of input signals; and an output portion arranged to provide a plurality of output signals corresponding to each of the demodulated input signals.

In a still further aspect of the present invention there is provided a unit for performing lock-in demodulation of a plurality of input signals comprising: an input portion arranged to receive a plurality of input signals; a sequential lock-in demodulation portion arranged to demodulate the plurality of input signals; and an output portion arranged to provide a plurality of output signals corresponding to each of the demodulated input signals.

Thus, apparatus according to embodiments of the invention is arranged to perform sequential lock-in demodulation of a linear array of sensing elements.

According to some embodiments of the invention there is provided apparatus for inspecting an engineering material or food product comprising: a controller arranged to generate a time-variant drive signal; a source of Near Infra-Red (NIR) radiation, the source being operable by the controller to emit a repetitive time-varying beam thereby to illuminate an article; and a detector, the detector being configured to detect that portion of the source beam that has been transmitted through at least a portion of the article, and to generate an electrical signal that has a time variant modulation corresponding to the modulation of said portion of the source NIR beam, the controller being further configured to generate an output corresponding to a variation in the amplitude of the received NIR source beam.

Embodiments of the invention may be understood with reference to the accompanying drawings in which FIG. 1 shows inspection apparatus according to an embodiment of the invention in which a diffuser element is provided downstream of an illumination source;

FIG. 2 shows an embodiment in which a collimator is provided in combination with an array of detectors;

FIG. 3 shows (a) a sample to be inspected being two prunes; (b) a 2D plot of detected illumination intensity as a function of position in a transmission mode of operation for the sample shown in (a) each prune having a pit; (c) a line scan across the plot shown in (b) at an arbitrary location from left to right; (d) a 2D plot of detected illumination intensity as a function of position in a transmission mode of operation for the sample shown in (a) where the left-hand prune has had its pit removed; and (e) a line scan across the plot shown in (d);

FIG. 16 illustrates an experiment in which objects concealed under clothing were detected from a distance of several meters;

DETAILED DESCRIPTION OF THE INVENTION

Figure 1:
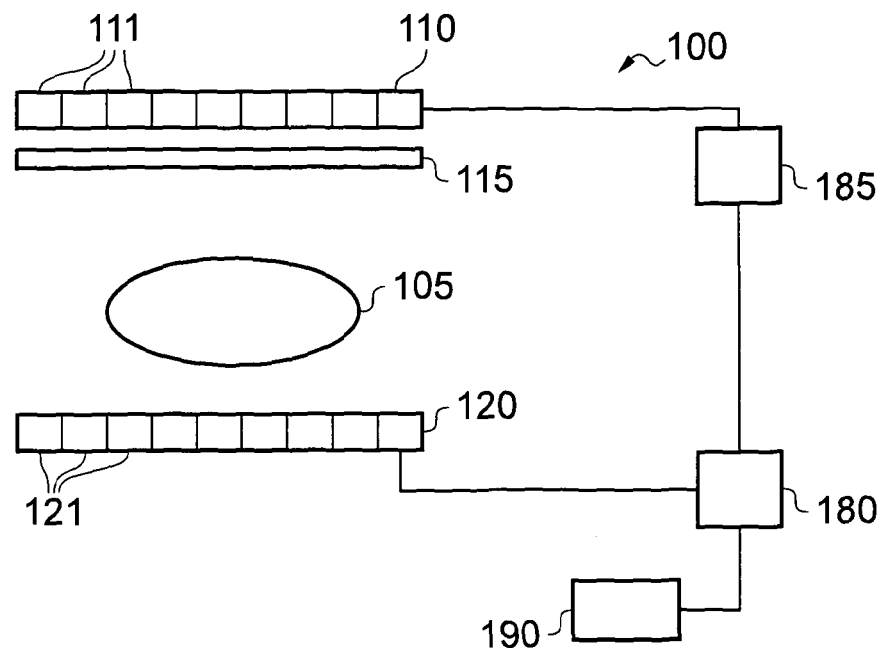

FIG. 1 shows inspection apparatus 100 for performing non-destructive evaluation of samples or objects 105. The apparatus 100 has a near infra-red (NIR) illumination source 110 comprising an array of light emitting photodiodes 111 arranged to project illumination (or radiation) onto a diffuser element 115. The diffuser element 115 is arranged to diffuse (or 'scatter diffusely') illumination from the source 110 such that illumination transmitted through the diffuser element 115 exits the element 115 at a plurality of different angles.

The apparatus 100 is also provided with a photodetector array 120 in the form of a linear array of photodetector elements arranged to detect an intensity of illumination incident thereon.

The source 110 is powered by a drive module 185, the module being arranged to power the source 110 such that the source emits radiation of an intensity that varies periodically as a function of time.

The drive module 185 is in communication with a lock-in amplifier module 190 to which an output from the photodetector array 120 is fed. The lock-in amplifier module 190 is fed a signal from the drive module 185 corresponding to the drive signal provided to the photodiode array 110.

It is to be understood that an alternative signal recovery technique may be employed in addition to or instead of the lock-in technique described here.

The output from the photodetector array 120 corresponds to an intensity of illumination incident on a selected photodetector 121 of the array 120.

In the embodiment shown, the lock-in amplifier module 190 provides a DC output corresponding to the intensity of illumination incident on a given photodetector 121 of the array 120.

The DC output from the lock-in amplifier module 190 is fed to a computing device 190 which is arranged to store values of intensity output from the lock-in amplifier module 190.

It is to be understood that by addressing each photodetector 121 of the array 120 in turn, a plot of intensity as a function of position across the sample 105 may be obtained.

The presence of the diffuser element 115 has the effect of increasing a contrast obtainable from an inspection of a given sample 105. In some examples, the presence of a diffuser element 115 is particularly effective in samples exhibiting a relatively high degree of scattering.

Figure 2:
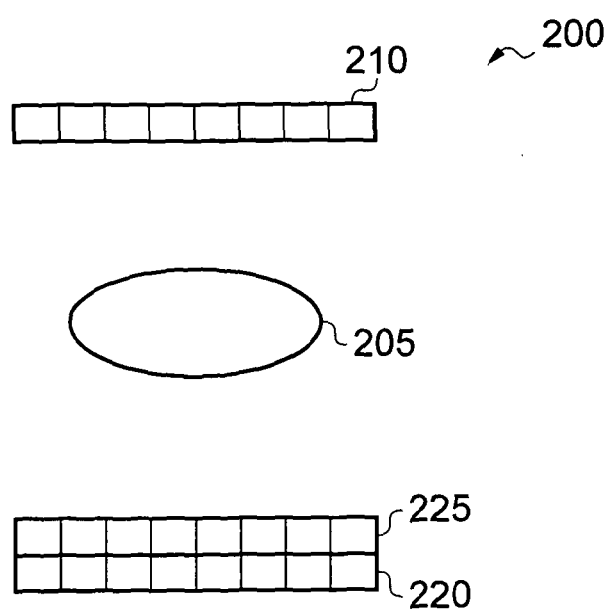

FIG. 2 shows an embodiment of the invention similar to that of the embodiment of FIG. 1. Like features of the embodiment of FIG. 2 to those of FIG. 1 are shown with like reference signs prefixed numeral 2 instead of numeral 1.

The embodiment of FIG. 2 is provided with a collimator 225 between the sample 205 and the photodetector array 220 instead of a diffuser element 115. The collimator 225 is arranged to reduce the range of angles with respect to the array 220 over which radiation from the source passing though the sample 205 is permitted to be incident upon the array 220.

This has the effect that the proportion of NIR radiation reaching the array 220 that has been scattered by the sample 205 is reduced. Thus, the proportion of NIR radiation detected by the array 220 that has been transmitted through the sample 205 with little or no scattering is increased.

Such an arrangement has the advantage that it increases the amount of contrast or the difference between an intensity of NIR radiation falling on the array 220 when a concealed object such as an inclusion or foreign object is in the path of the beam through the sample and the intensity when the concealed object or foreign object is not in the path of the beam.

In some embodiments having a collimator 225 as in the embodiment of FIG. 2 a diffuser element 115 may also be provided in a similar manner to the arrangement of the diffuser element 115 and illumination source 110 of the embodiment of FIG. 1.

Figure 3A:
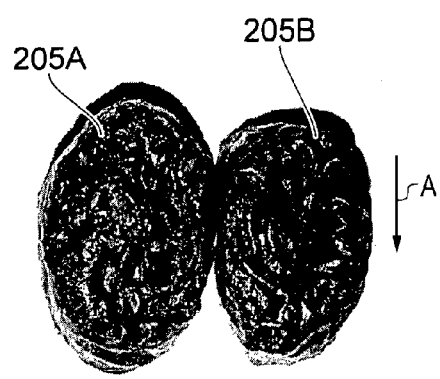

FIG. 3(a) shows a sample that was subject to analysis using apparatus 100 according to an embodiment of the invention operated in a transmission mode. The sample consisted of a pair of prune fruits 205A, 205B.

Figure 3B:
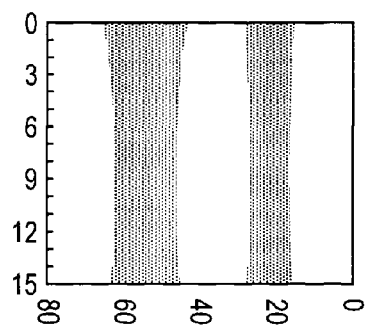

FIG. 3(b) shows a plot of intensity as a function of position obtained by scanning a linear photodiode array over the sample along a direction normal to a longitudinal axis of the array as the sample was moved past the array in a direction parallel to arrow A, the array being oriented parallel to a direction normal to the arrow and in the plane of the page.

Figure 3D:
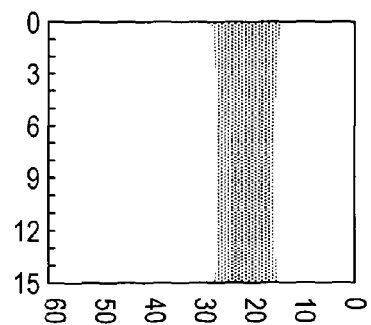
Figure 3C:
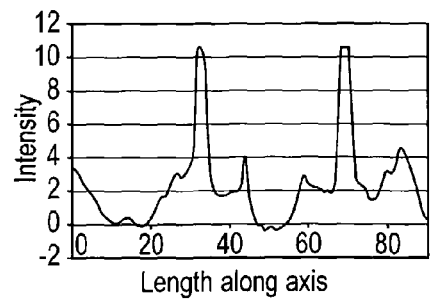
Figure 3E:
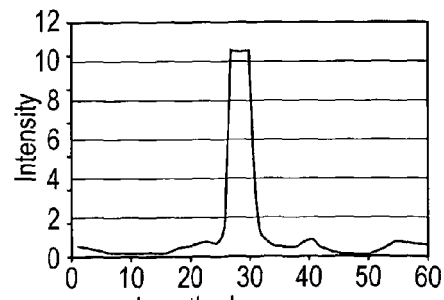

FIG. 3(c) shows a line scan across the plot of FIG. 3(b). Each of the prunes had a pit within the fruit. The pit is responsible for the streaks of decreased intensity (darker regions) in the plot that run from the top to the bottom of the plot.

FIGS. 3(d) and (e) are corresponding plots to those of FIGS. 3(b) and (c) obtained after removing the pit from the left hand prune 205A. It can be seen that only one substantial dark streak is now present in the plots. This is because the pit scatters/absorbs more illumination than the flesh of the fruit, resulting in a region of decreased intensity of illumination transmitted through the sample.

It is to be understood that embodiments of the invention are useful in performing non-destructive and non-invasive testing of samples.

Figure 4:
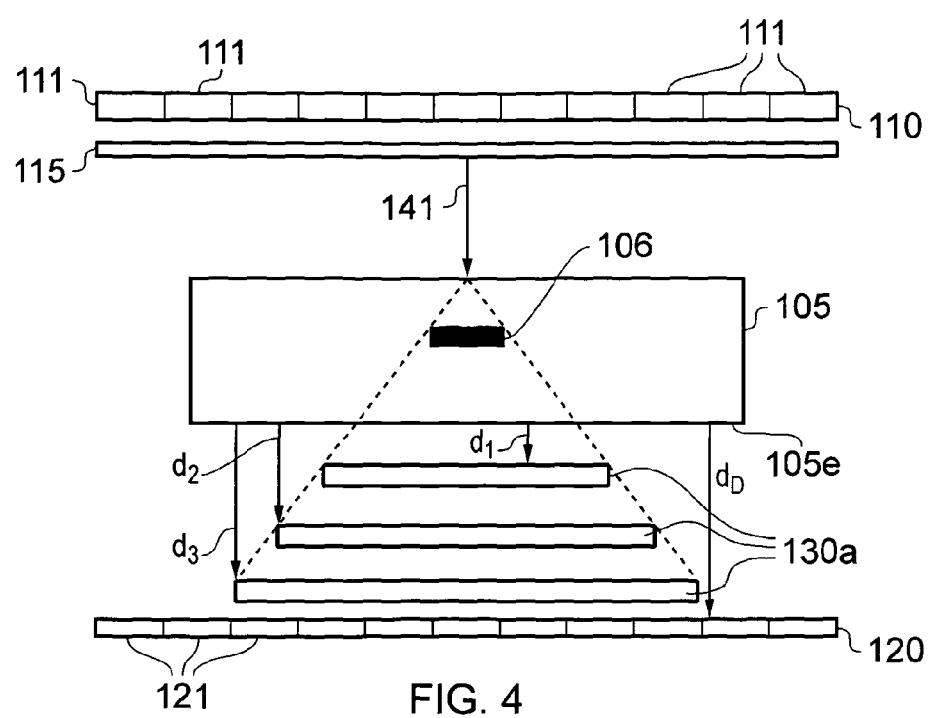
FIG. 4 shows a side-view of an arrangement showing an increase in a size of a shadow cast be a scattering object as distance from an exit face of a sample increases.

FIG. 4 shows apparatus according to the embodiment of FIG. 1 in which the light emitting photodiode array 110 is arranged to generate a beam 141 of NIR radiation that irradiates an article 105.

It can be seen that the article 105 has an inclusion 106 therein that causes scattering of NIR radiation passing through the article 105 that is incident on the inclusion 106. The article 105 may for example be in the form of a matrix of a host material (such as a cheese) having an inclusion 106 therein in the form of a foreign body being a material other than the host material (such as a piece of plastics material, a textile material or any other material). For the purposes of the present discussion the inclusion 106 may alternatively be a light scattering or light absorbing defect such as a void or a region of the matrix that is of a similar material but of a different composition to that of a neighbouring region of the matrix, for example a region of a cheese of different composition to another region of the cheese.

It is found that the presence of the inclusion 106 may cause a 'shadow' to be cast by the inclusion 106 on the photodetector array 120. A distance dD between the inclusion 106 and detector array 120 determines the size (in lateral extent and area) of the shadow that is cast.

It is to be further understood that the size of the shadow cast by the inclusion 106 is typically larger than the size of the inclusion itself. Increasing the distance dD typically results in an increase in the size of the shadow cast on the detector array 120, enhancing an ability to detect the inclusion 106.

Thus it is to be understood that in some embodiments inclusions that are smaller than a distance between photodetectors 121 of the photodetector array 120 may still be reliably detected. That is, the shadow cast by the inclusion 106 may be greater than the distance between photodetectors 121 such that the shadow is too large to fall entirely between photodetectors 121. This reduces a risk that an inclusion 106 escapes detection when the article 105 is inspected.

In some arrangements it may be advantageous to employ a point source of illumination such as a laser beam or other beam in order to increase an amount of contrast in the intensity of light incident on the array 120 due to the presence of the inclusion 106.

The point source may be arranged to generate a fan-type source (see below). The fan-type source may be arranged to generate a beam of radiation that is narrow in azimuth and broad in elevation.

Figure 5A:
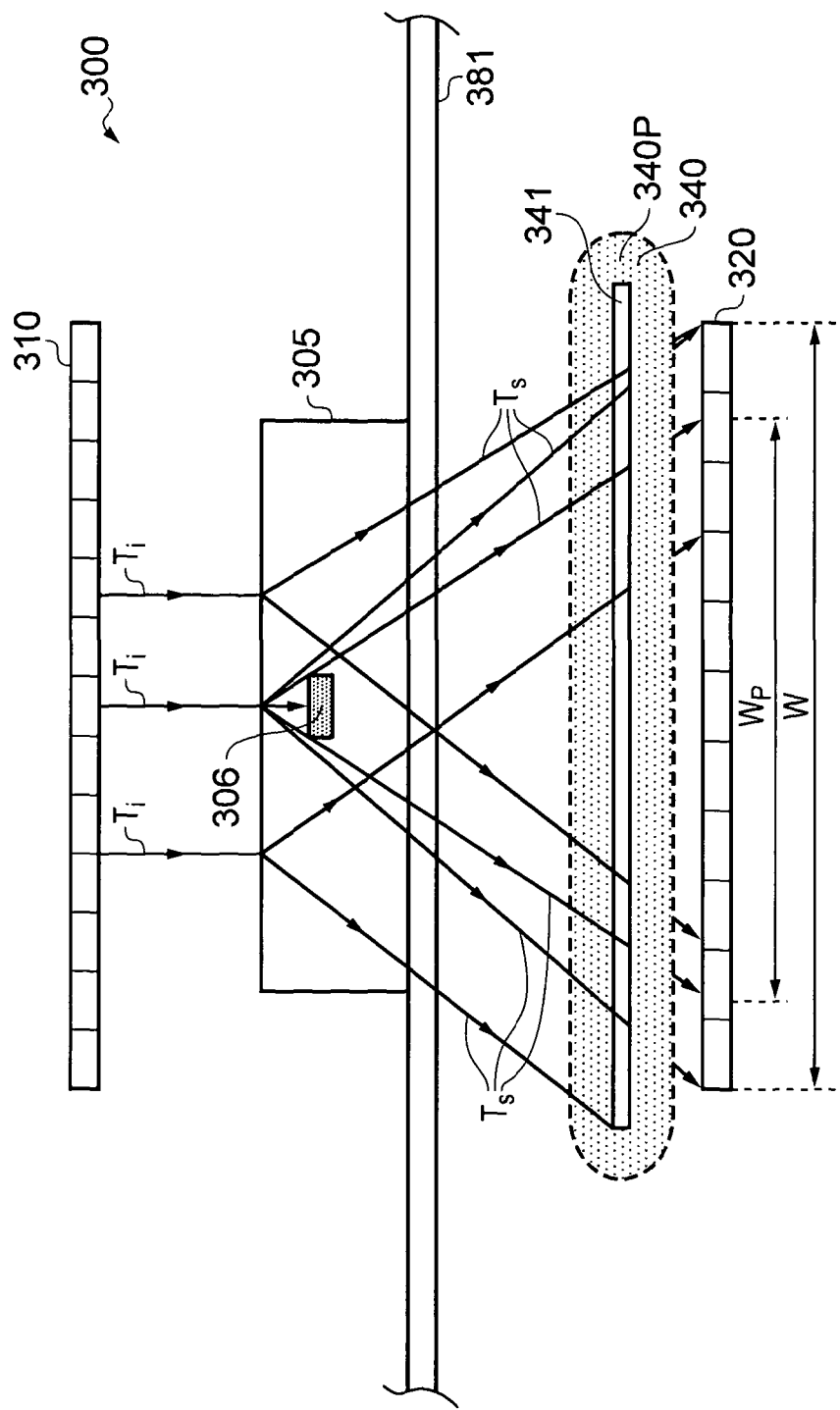
FIG. 5 shows apparatus according to an embodiment of the invention having a conveyor belt in (a) cross-section along a direction parallel to a direction of travel of the conveyor and (b) cross-section normal to a direction of travel of the conveyor, and (c) a collimator and detector arrangement for use in embodiments of the invention.
Figure 5B:
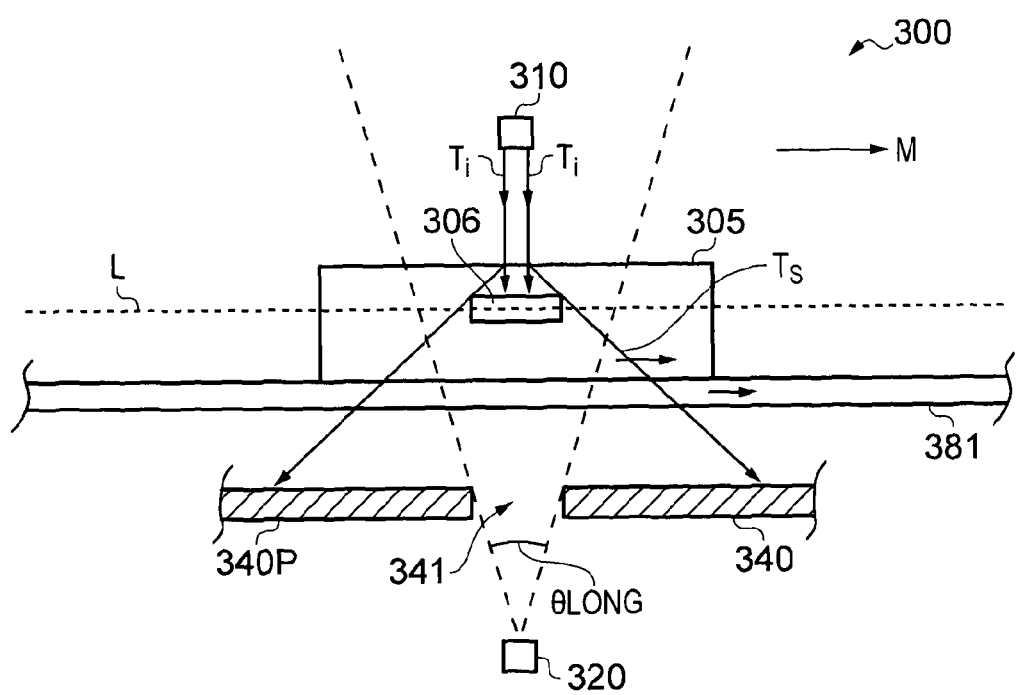

Thus, in respect of the coordinate system of FIG. 5(*c*), in some embodiments the beam may have a relatively large lateral angle of divergence θLAT (with respect to an orientation of the article) but a relatively narrow longitudinal divergence θLONG with respect to the orientation of the article.

The fan-type source may have a lateral angle of divergence of around 30 to 60 degrees. The longitudinal angle of divergence many be in the range of from around 5 to around 30 degrees. In some arrangements the longitudinal angle of divergence may be in the range from around 5 to around 25 degrees, from around 5 to around 20 degrees, from around 1 to around 10 degrees, from 1 to around 20 degrees or any other suitable value. The lateral angle of divergence may be greater than the longitudinal angle of divergence by a factor of from around 2 to around 10 or more, optionally around 2 to around 5 or more.

In some arrangements the lateral and longitudinal angles of divergence of the source are both in the range from around 30 to 60 degrees.

In some arrangements the lateral and longitudinal angles of divergence of the source are substantially the same as one another.

Other arrangements are also useful.

Illumination with a fan-type source can enhance a contrast between a shadowed region of the detector array 120 and a non-shadowed region since a reduced amount of light that has not been scattered by the inclusion 106 may be incident on the shadowed region. It is to be understood that the greater the longitudinal angle of divergence the larger the amount of radiation scattered by a region away from the region between the source and the detector that may be incident on the detector, thereby reducing an amount of contrast in the intensity of light incident on the detector array that has been scattered only by an article or portion of an article directly between the source and detector array.

Thus in some embodiments it is advantageous to employ a fan-type source having a longitudinal angle of divergence that is sufficiently small to illuminate substantially only a region of the article between the source and detector such that substantially only light transmitted directly through the sample without being scattered by the article and/or other medium between the source and detector is directly incident on the detector.

Thus an amount of light that is incident on the sample in a direction such that direct transmission of the light though the sample would not result in detection of the light is reduced whereby an amount of light travelling in such a direction that is scattered and then detected by the detector is reduced.

It is to be understood that a turbid host medium being a medium such as a cheese or a milky fluid is by definition highly scattering and illumination of the medium with a single collimated point source of illumination (such as a laser beam) rather than the relatively wide and substantially continuous beam of the arrangement of FIG. 4 can be advantageous in some arrangements. It is to be understood that when a turbid medium is irradiated with radiation a much larger internal volume of the medium may be exposed to laser illumination (due to scattering of the radiation) than might otherwise be the case for a substantially transparent medium where an amount of light scattering is negligible or low.

FIGS. 5(*a*) and (*b*) show inspection apparatus 300 according to a further embodiment of the invention. Like features of the embodiment of FIGS. 5(*a*) and (*b*) to those of the embodiment of FIG. 4 are shown with like reference signs prefixed numeral 3 instead of numeral 1.

FIG. 5(*a*) shows the apparatus 300 as viewed parallel to a direction of travel M of the article 305 (as shown in FIG. 5(*b*) by arrow M).

FIG. 5(*b*) shows the apparatus 300 as viewed along a direction normal to the direction of travel of the article 305, which is shown travelling from left to right in the direction of arrow M.

The apparatus 300 has a linear photodiode array 310 arranged to illuminate articles 305 on a conveyor belt 381 passing under the array 310 in the direction of arrow M. In the arrangement shown the photodiode array 310 is positioned above the conveyor belt 381. A corresponding linear photodetector array 320 is provided underneath the belt 381.

The optical arrangement of the apparatus 300 differs from that of FIG. 4 in that the apparatus 300 also has a collimator 340 between the sample 305 and the detector array 320. The collimator 340 is a slit-type collimator having an elongate aperture or slit 341 formed in an opaque plate 340.

The collimator 340 is arranged such that the aperture 341 is oriented substantially parallel to the light emitting photodiode array 310 and to the array of photodetectors 320, being provided therebetween such that the light emitting photodiode array 310 and the array of photodetectors 320 are in a direct line of sight of one another through the aperture 341.

FIG. 5(*c*) illustrates schematically the manner in which the collimator 340 is able to block light selectively thereby to enhance a contrast between signals detected by the photodetector array 320 in the presence and absence of an inclusion 306 or other defect or foreign body in, on or under an article 305 under inspection. An imaginary line N normal to the photodetector array 32 and passing through a centre of the aperture 340 is shown in FIG. 5(*c*) for ease of reference.

It can be seen that a lateral acceptance angle θLAT of the photodetector array 320 to light entering the aperture 341 of the collimator 340 and travelling in a plane A in which the detector array 320 lies is larger than a longitudinal acceptance angle θLONG of the photodetector array 320 to light entering the aperture 341 of the collimator 340 and which travels in a plane B normal to the detector array 320 by virtue of the fact that the aperture 341 is elongate.

Figure 5C:
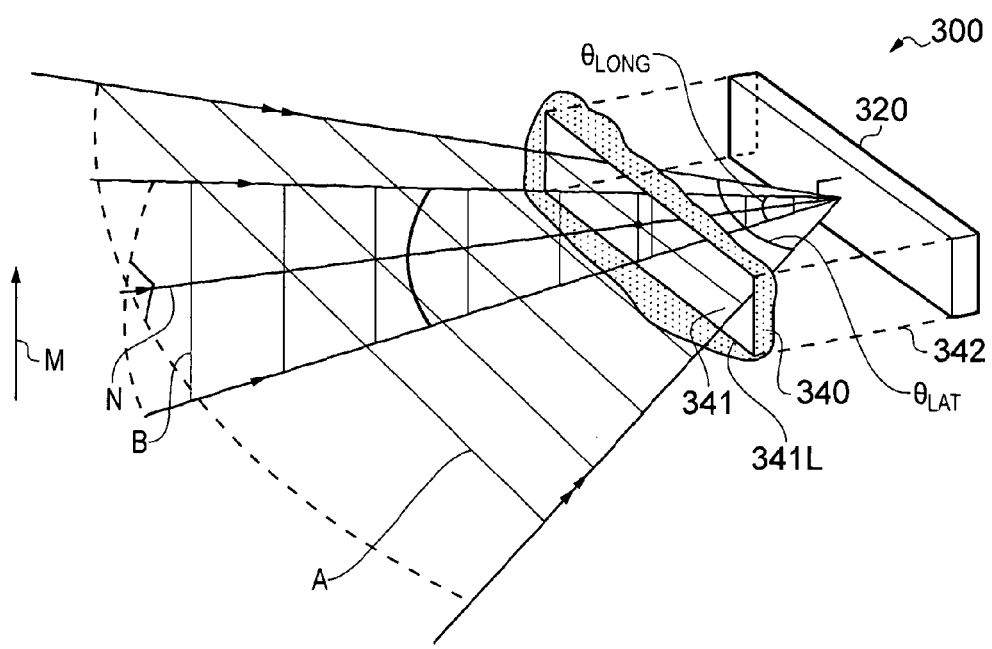

Two rays of light travelling in plane A are shown with double arrows whilst two rays of light travelling in plane B are shown with single arrows in FIG. 5(c).

It is to be understood that the lateral acceptance angle θLAT is arranged to be sufficiently large to accept light scattered across a full lateral extent of interest of the article that is to be inspected whilst the longitudinal acceptance angle θLONG is arranged to be sufficiently narrow to enable a location of an inclusion or foreign body above or below the article to be determined to a required precision with respect to a line parallel to a direction of movement M of the article relative to the detector 320.

In some embodiments θLAT is around 60 degrees and θLONG is around 2 to 6 degrees. Other values are also useful.

This feature has the advantage that a contrast at the detector 320 between a region of the detector 320 shadowed by an inclusion 306 within the article 305 (or another foreign body above or below the article 305) and a region not shadowed by the inclusion 306 or other foreign body may be increased.

Furthermore, this feature also has the advantage (as noted above) that a position of the inclusion 306 or other foreign body may be determined as being substantially within the volume of the sample 305 between the photodiode array 310 and the array of photodetectors 320 thereby giving relatively highly localised information in respect of the spatial location of the inclusion 306 in the direction of travel of the article 305.

Thus, if the apparatus 300 detects the presence of an inclusion 306 (or any other undesirable scattering object between the photodiode array 310 and photodetector array 320) an eject mechanism may be arranged to eject the article 305 from the conveyor or to reject the article 305 by some other means downstream of the apparatus 300.

It is to be understood that optionally the collimator 340 may have a conduit 342 that is opaque to NIR radiation (such as a metallic conduit) provided between the aperture 341 and the photodetector array 320. The purpose of the conduit may be to prevent light reaching the detector array 320 that is not passing through the entrance aperture 341 in a direct path to the detector array 320. That is, to prevent light from reaching the detector array 320 that has not passed through the aperture 341 and to prevent light reaching the detector array 320 that has been scattered after passing through the aperture 341.

Thus the presence of the conduit 342 has the advantage of reducing a risk that light scattered through the aperture 341 not on a trajectory to become incident on the detector 320 is scattered such that it does become incident on the detector 320.

It is to be understood that in some arrangements the presence of the conduit 342 reduces extraneous illumination of the detector array 320 thereby enhancing an ability of the apparatus to detect concealed objects.

The conduit 342 may be in the form of a tube of rectangular cross-section, optionally having a non-reflective coating on an inner surface thereof. In some arrangements the inner surface may be a black surface. Other arrangements are also useful depending on the shape and size of the detector array. Thus if a single detector is employed (rather than an array) the conduit 342 may be of a different shape. Similarly, if the detector array is a 2D array the conduit 342 may be of a corresponding cross-section.

In FIGS. 5(a) and (b) the article 305 is shown located directly above the slit 341 in the collimator 340. It can be seen that beams of light Ti incident on the article 305 are scattered by the article 305 forming scattered beams Ts.

A light-absorbing and/or light scattering inclusion 306 in the article 305 causes a portion Wp of a length W of the photodetector array 320 to be shadowed by the inclusion 306. It is to be understood that by virtue of the shadowing effect of the inclusion 306, the portion Wp of the detector array 320 that is shadowed by the inclusion 306 is much larger in lateral extent than the inclusion 306 itself.

Although the region of the detector array 320 shadowed by the inclusion 306 may still receive some illumination by light scattered by other regions of the article 305, a detectable decrease in light intensity at the detector array 320 occurs due to the presence of the inclusion 306.

As note above, in the embodiment of FIGS. 5(a) and (b) the collimator 340 is in the form of a plate 340P having an aperture 341 in the form of a slit formed therein.

Figure 6:
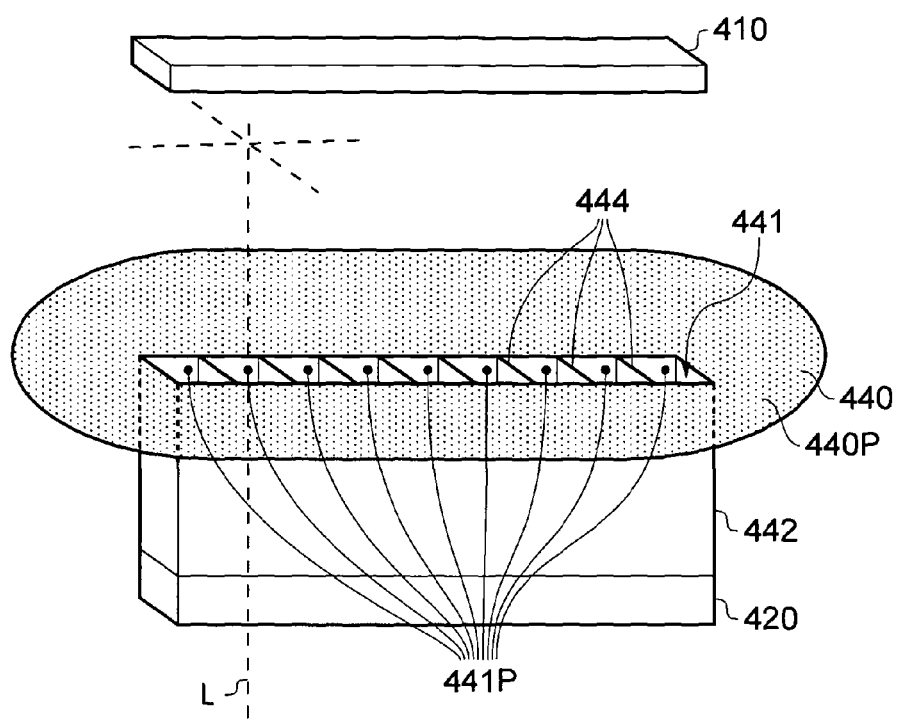
FIG. 6 shows an alternative collimator and detector arrangement.

FIG. 6 shows an alternative collimator 440 suitable for use with apparatus according to embodiments of the present invention. The collimator has a plate 440P formed from a material opaque to NIR radiation such as a metallic plate and has an aperture 441 formed therein. The aperture 441 is arranged to allow light therethrough to a photodetector array 420 via a conduit 442 defined by a continuous wall. The wall of the conduit 442 is also formed from a material opaque to NIR radiation such as a metallic material.

A series of opaque baffle plates 444 are provided within the conduit 442 between major opposed walls thereby to define an array of parallel light pipes 541P within the conduit 442. It is to be understood that the light pipes 541P are arranged to limit lateral and longitudinal acceptance angles θLAT, θLONG of the photodetector array 420 in a similar manner to the collimator 340 of FIGS. 5(a) and (b). However it can be seen that the lateral acceptance angle θLAT will be of a similar size to the longitudinal acceptance angle θLONG in the embodiment shown although other arrangements are also useful.

In some embodiments θLAT and θLONG are around 2 to 6 degrees.

Thus, light passing through a given light pipe 541P is limited to light that enters a given light pipe 541P travelling along a direction substantially parallel to the longitudinal axis L of the light pipe 541P. Such a collimator 440 may be referred to as a 'push-broom' collimator.

As noted above, in the embodiments described the light emitting photodiode arrays 110, 210, 310, 410, 510 and photodetector arrays 120, 220, 320, 420, 520 are both linear detector arrays having a 1D array of light emitting photodiodes and photodetectors respectively. It is to be understood that the arrays may alternatively be of any suitable form. For example in some arrangements only a single light emitting photodiode may be employed and/or a single photodetector. In some arrangements a 2D array of light emitting photodiodes and/or photodetectors may be employed.

As noted above in some embodiments an autocorrelation, lock-in or other small signal recovery technique is used. Thus the intensity of NIR radiation is modulated in a periodic manner.

In some arrangements an autocorrelation or other lock-in technique is employed. In some embodiments a heterodyning technique is employed. In some embodiments a homodyning technique is used. In some arrangements a tuned circuit is employed not implementing lock-in, autocorrelation or cross-correlation techniques. In some embodiments an independent tuned circuit is employed.

The tuned circuit may comprise an AC coupled amplifier with a passband response which has a passband width tailored to be as narrow as required by a given application. The passband is arranged to be centred on the frequency of modulation of the source of NIR radiation and to increase the signal to noise ratio (SNR) of the received signal.

It is to be understood that the small signal recovery technique may be employed to substantially eliminate variations in background intensity of an image, due for example to variations in density, thickness and/or microstructure of an article. This allows inclusions and other foreign bodies or defects in or on the article to be detected more reliably. That is, inclusions, foreign bodies or defects in or on a matrix provided by the article may be detected more reliably.

In some alternative embodiments a wavelength of NIR radiation from the source is changed in a periodic manner, for example by employing light-emitting photodiodes emitting different respective wavelengths, for example 850 nm and 940 nm respectively.

The intensity of radiation of the one or more wavelengths transmitted through at least a portion of the article is then detected by means of the detector. A small-signal recovery technique is employed to distinguish the portion of the signal detected by the detector that is due to the source from other background illumination based on the variation in wavelength and/or intensity.

In the case that the wavelength is changed, in some arrangements the detector may be configured to detect NIR radiation in a prescribed wavelength band or range and the wavelength of NIR radiation modulated so that it changes from a value within this band to a value outside this band in a periodic or other alternating manner. The detector may have one or more portions arranged to make measurements of radiation intensity falling on the detector in respective different wavelength bands or ranges thereby to determine the amounts (such as absolute or relative amounts) of radiation of each wavelength range falling on the detector.

In some embodiments interlaced video images of rapidly alternating NIR wavelength changes and/or rapidly changing intensities of NIR radiation of a given wavelength are obtained in order to eliminate variations in background density, thickness and microstructure of the embedding matrix in order to enhance detection of embedded objects. Thus respective sequential frames may be recorded at different respective intensities and/or wavelength of incident radiation.

In some embodiments known windowing functions and enhancement techniques for example techniques used in video processing based on histogram distributions of pixel values may be used as a method of detecting embedded objects.

The techniques may be employed to detect the presence of inclusions, foreign bodies or other defects in a non-imaging manner, i.e. without an intention or requirement to generate an image of an article or portion thereof.

Thus embodiments of the invention may be distinguished from relatively simple thresholding techniques where detection of a concealed object or the like is made with respect to the intensity of a signal detected by the detector.

For example, in some such techniques, if the intensity is above or below a given threshold the apparatus determines that a concealed article or the like may be present. Such a technique has the disadvantage that a false determination of the presence or absence of a concealed article may be made.

In some arrangements the apparatus is arranged to perform a correlation of signal intensity across an image and to determine whether a sufficiently large region of the image exists in which an intensity of NIR radiation is above or below a prescribed threshold thereby to determine whether or not a concealed object may be present in the article.

Thus in some embodiments histogram equalisation is employed to sharpen a contrast in received data, for example a substantially one dimensional line scan or a substantially 2D 'image' that may be obtained from a camera or other array of photodetectors. The 2D image may be obtained for example by moving the article with respect to a 1-D array of photodetectors and recording detected intensity as a function of article position.

The apparatus may be arranged to perform histogram equalisation to sharpen contrast in the data recorded from the detector. The apparatus may then be arranged to analyse a distribution of values of intensity of data points (such as 'pixels') obtained from a given region of a line-scan or area of a 2-D array of data points in order to distinguish between background noise and concealed articles.

Figure 7:
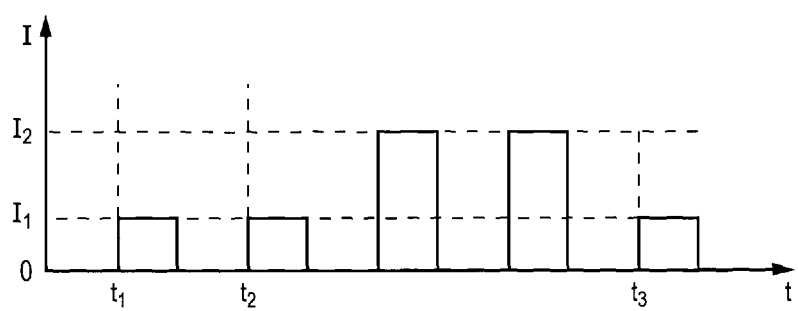
FIG. 7 is a schematic illustration of a profile of an intensity of illumination emitted by a source in apparatus according to an embodiment of the invention.

FIG. 7 shows an intensity profile of a modulated beam of NIR radiation generated by a source in apparatus according to an embodiment of the invention.

The beam comprises a series of square waves of period t2-t1, the square waves themselves having a periodic amplitude variation of period (t3-t1). A first pair of square waves are of amplitude I1 whilst a second pair of square waves are of amplitude I2 where I2 is greater than I1.

It is to be understood that waves other than square waves may be employed. Similarly other intensity variations are useful.

The apparatus is configured to employ a small signal recovery technique to produce a DC signal corresponding to the amplitude of the square wave signal detected by the detector.

The apparatus may be configured to employ either data corresponding to the signal of lower intensity or data corresponding to the signal of higher intensity in order arranged to detect determine whether an inclusion is present. The apparatus may be arranged to determine whether to use the signal of lower or higher intensity responsive to the intensity of detected radiation. In the event that the article is relatively thin and the detector is at or close to saturation, the apparatus may be arranged to employ the signal of lower intensity.

This feature has the advantage that problems associated with saturation of the detector, for example due to a relatively thin article, whereby the apparatus may fail to detect an inclusion may be avoided.

It is to be understood that in some embodiments an article is arranged to be irradiated with radiation of more than two different respective intensities thereby to further reduce a risk of saturation of a detector.

Furthermore, where an amount of radiation that is transmitted through an article varies due for example to a variation in thickness of the article, the fact that radiation of different intensities is directed at the sample allows the apparatus to employ different intensities when inspecting different portions of the sample.

Thus, the apparatus may be arranged to employ signals corresponding to radiation of different respective intensities when imaging different respective regions of a sample responsive to the intensity of radiation detected from a given region of a sample.

Figure 8:
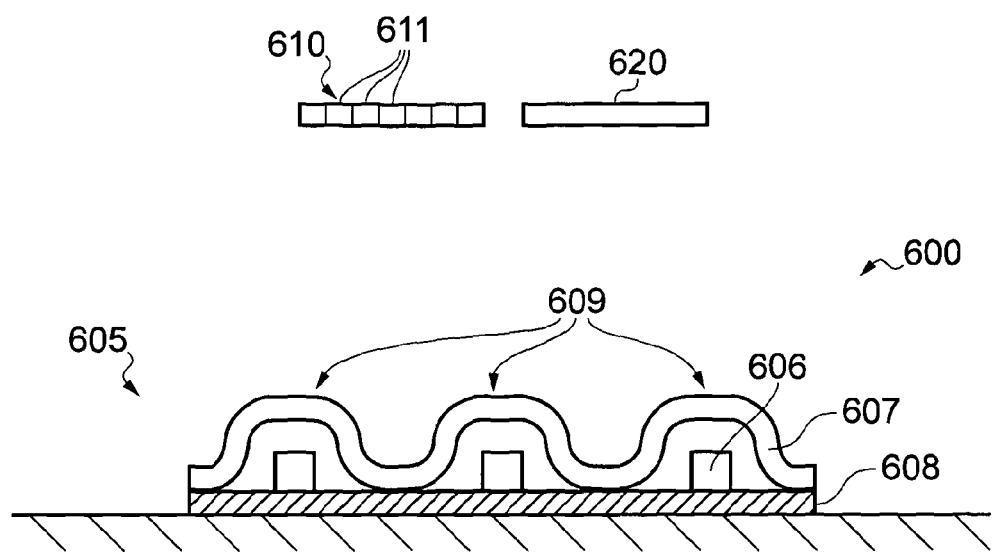
FIG. 8 shows an embodiment in which apparatus according to an embodiment of the invention is arranged to detect radiation that has passed through a sample and been scattered back through the sample by means of a reflector member.

FIG. 8 shows inspection apparatus 600 according to an embodiment of the invention having an illumination source 610 in the form of an array of photodiodes 611 arranged to emit NIR radiation. A photodetector array 620 is arranged to detect NIR radiation from the source 610 that is scattered by an object 605 back towards the photodetector array 620.

In the configuration shown the object is a blister pack 605 of tablets 606 and the apparatus 600 is arranged to detect NIR radiation scattered (or 'reflected') by a metallic foil 308 of the blister pack 305.

The blister pack 305 has a polymer sheet 307 defining an array of receptacles 609 in each of which a tablet 606 is provided. The foil 608 is bonded to the sheet 607 to seal the tablets 606 within the receptacles 609.

The blister pack 605 is oriented with the polymer sheet 607 towards the source 610 such that NIR radiation from the source 610 must pass through or between the tablets 606 before being reflected by the sheet 608.

It is to be understood that if the blister pack 605 is moved laterally relative to the linear source 610 and linear detector array 620 the amount of NIR radiation reflected back from the object 605 and detected at a given location of the detector array 620 will vary depending on whether the radiation is passing through a tablet 606 or not.

It is to be understood that movement of the article may not be necessary in the case where a sufficiently large 2D area detector is employed.

It is to be understood that by measuring a variation in reflected intensity as the pack 605 is moved it can be determined whether a tablet 606 is missing from a receptacle of a pack 605. For example, a periodic variation in detected intensity as the tablets 606 pass under the source 610 and detector array 620 may be interrupted when a tablet 606 is absent or other variation in structure of the object 605 is present. For example if more than one tablet 606 is present in a given receptacle the periodic variation may also be interrupted.

In some embodiments the apparatus 600 may be arranged to detect foreign bodies in tablets 606. In some embodiments the apparatus 600 may be arranged to monitor a composition of a tablet 606 and/or to determine whether a tablet is of a permitted type or not, for example whether a batch of tablets 606 has been contaminated with foreign bodies such as tablets 606 of a different type. Some embodiments may also be able to detect whether a tablet has maintained its structural integrity, for example whether it is still in one piece and not broken.

Embodiments of the invention may be arranged to detect markings or a shape such as the shape of the tablet 606 or other object thereby to determine whether the tablet 606 corresponds to a permitted type of tablet 606 or object.

It is to be understood that the arrangement of FIG. 8 may employed with apparatus 600 similar to that described above, for example with respect to the apparatus of FIG. 1 to FIG. 7, arranged to detect reflected radiation, or with apparatus not having a diffuser and/or collimator.

It is to be understood that some embodiments of the invention allow inspection of a sample by a beam of NIR radiation that also passes through an object or medium such as a conveyor belt before or after passing through the sample and before being received by a detector. It is to be understood that this is possible because certain materials from which a conveyor belt may be fabricated are sufficiently transparent to allow passage of NIR radiation therethrough. Thus, embodiments of the invention may be integrated into industrial facilities such as an industrial production line in a more convenient and less intrusive manner. Furthermore, an advantage of NIR imaging over X-ray imaging is that there is a reduced risk of damage or other unwanted effects on a sample such as a chemical change to an active ingredient of a pharmaceutical.

It is to be understood that where a detector is located on an opposite side of a conveyor to the article the conveyor belt or other conveyor employed in or with embodiments of the present invention must be formed from a material that allows NIR radiation to be transmitted therethrough, for example a material that is transparent to NIR radiation or a material that is translucent to NIR radiation.

It is to be understood that some embodiments of the invention may employ a fan-type source of NIR radiation arranged to generate a beam of radiation that is narrow in azimuth and broad in elevation. In respect of the coordinate system of FIG. 5(*c*), the beam may have a relatively large lateral angle of divergence (with respect to an orientation of the article) but a relatively narrow longitudinal divergence with respect to the orientation of the article.

The fan-type source may have a lateral angle of divergence of around 30 to 60 degrees.

In some arrangements the lateral and longitudinal angles of divergence of the source are both in the range from around 30 to 60 degrees.

In some arrangements the lateral and longitudinal angles of divergence are substantially the same as one another.

Other arrangements are also useful.

In one aspect of the invention apparatus is provided that is arranged to receive an optical signal, the apparatus having an optical splitter portion arranged to split the optical signal thereby to direct the optical signal along two spatially separate paths for the purpose of simultaneous analysis of the signal by different respective devices. The paths may be mutually orthogonal, mutually parallel or arranged at any other suitable angle to one another.

The splitter portion may be arranged to split the optical signal along more than two spatially separate paths.

Figure 9:
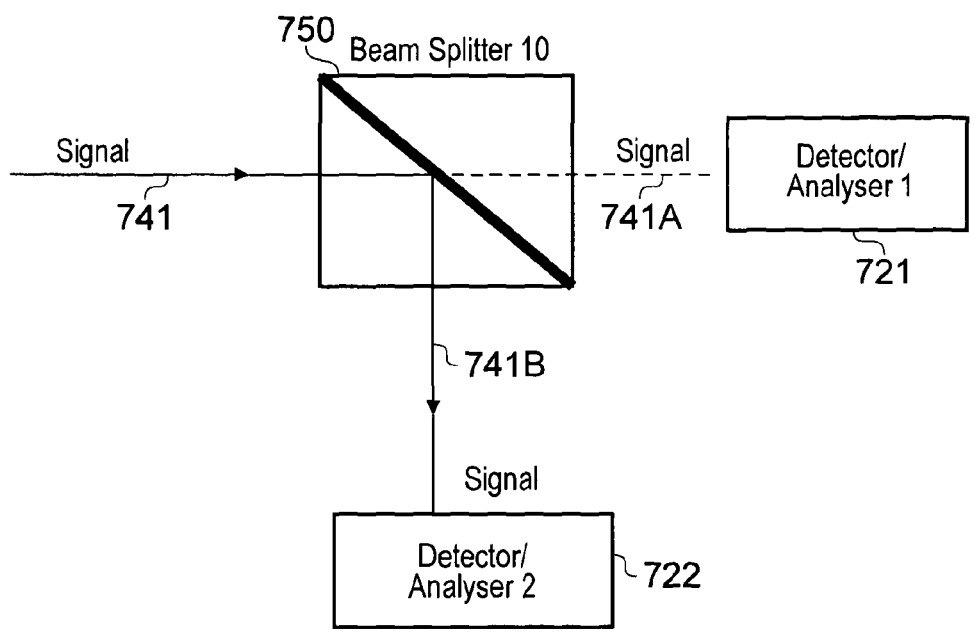
FIG. 9 shows a dual detector arrangement employing a beam splitter to split an incident beam between two detectors.
Figure 10:
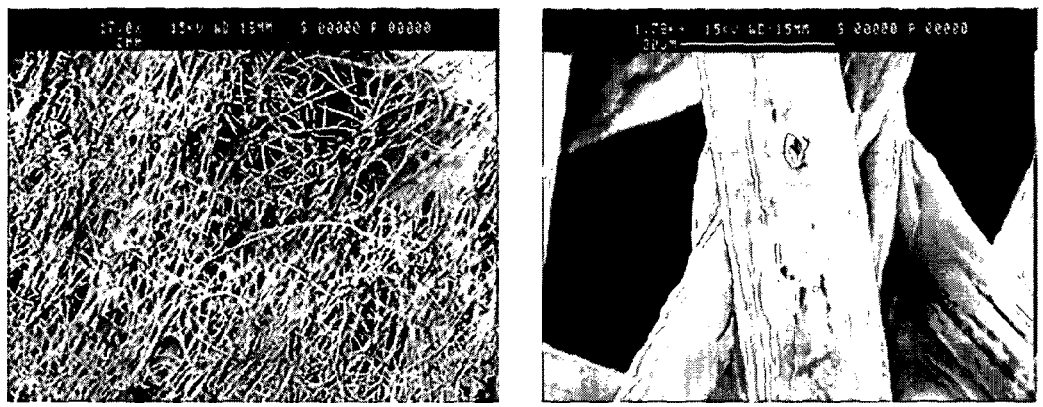
FIG. 10 is an electron micrograph of a microstructure of natural wool.

FIG. 9 shows a portion of apparatus according to an embodiment of the invention in which a beam splitter 750 is arranged to split an incoming beam of optical radiation 741 from an article into two spatially separate (and in this case mutually orthogonal) paths 741A, 741B.

A first path 741A is directed towards a first detector or analyser 721 whilst a second path 13 is directed towards a second detector or analyser 722.

Such an arrangement has the advantage over alternative arrangements that parallax is eliminated regardless of the magnitude of a distance between the detectors 721, 722 and the article being imaged.

For example, if the first detector 721 is a spectrometer and the second detector 722 is a video camera then chemical data obtained by means of the spectrometer 721 may be arranged to correspond to an article or portion of an article in the field of view of an image generated by the video camera. For example the chemical data may be arranged to correspond to an article at the centre of the image.

In one embodiment the first detector 721 (detector 1) is a spectrometer and the second detector 722 (detector 2) is a video camera sensitive to the near infra-red (NIR) part of the spectrum. This allows us to simultaneously superimpose the chemical information on top of a normal video image in a data fusion approach; that is, an image appears on the screen, the area/subject of interest can be zoomed in on and enlarged and a representation of a chemical spectrum appears on the screen 'underneath' (i.e. superimposed on) the image.

This allows real-time standoff detection of explosives and other substances concealed under clothing to be made. The apparatus allows signals corresponding to explosives and other substances to be integrated into standard video images via a data fusion process as will be described in detail below.

It is to be understood that in some embodiments of the invention apparatus described above in respect of FIG. 1 to FIG. 8 may be employed with the splitter 750, the apparatus being arranged to detect an optical signal passing along one of the first or second paths 741A, 741B.

Alternatively, it is to be understood that in some embodiments of the invention apparatus described in WO 2008/001141 may be arranged to detect an optical signal passing along one of the first or second paths 741A, 741B. Thus, a modulated beam may be used to illuminate the subject, enabling detection of concealed objects.

The content of WO 2008/001141 is hereby incorporated by reference.

Apparatus according to embodiments of the invention may be arranged to detect an optical signal at one or more prescribed wavelengths in order to obtain chemical information about an object.

In some embodiments apparatus described in WO 2008/001141 is provided to detect an optical signal passing along the first path 741A and apparatus described in WO 2008/001141 is provided to detect an optical signal passing along the second path 741B.

Other configurations are also possible. For example, the first and/or second detectors 721, 722 could be anything that light affects, such as two different cameras, one arranged to detect ultra-violet (UV) light and the other arranged to detect infra-red (IR) light. In some embodiments the first and second detectors 721, 722 could be different types of spectrometer for different parts of the spectrum.

In some embodiments one of the detectors is a spectrometer and the other is a camera.

In some embodiments the apparatus is modular, allowing different devices or apparatus to be coupled to the beam splitter 750 to receive an optical signal passing along an optical path 741A, 741B. Thus, at one moment in time spectral analysis could be performed on an optical signal passing along the first or second path 741A, 741B by means of a conventional spectrometer device, and subsequently analysis could be performed using a bespoke Lock-In device such as one described in WO 2008/001141 by replacing the conventional device with the bespoke device. In some embodiments the conventional device is arranged to receive an optical signal passing along one optical path 741A, 741B and the bespoke device is arranged to receive an optical signal passing along the other optical path 741A, 741B.

The beam splitter 750 could be a dichroic filter or a part silvered mirror etc and could even extend to other parts of the spectrum—possibly as far as soft x-rays in one direction and up to Terahertz frequencies in the other.

Embodiments of the invention suitable for enabling real-time standoff detection of explosives and other substances concealed under clothing to be made will now be described.

A novel and low-cost technique of standoff detection is presented that permits the detection of explosives and other contraband substances that are hidden under clothing at standoff distances. The technique uses NIR beams of wavelengths found in ordinary domestic remote controls apparatus, combined with various signal recovery techniques commonly used in astronomy.

This alternative technique, whilst sophisticated, utilises readily available optoelectronic components. It is inherently far more portable than currently available commercial alternatives and is easy to use. A pre-production prototype successfully detected and identified the common homemade explosives ammonium nitrate and hydrogen peroxide, which were concealed behind clothing from a distance of 5 meters under daytime (daylight) conditions. In principle, this distance could be extended as far as 50 meters without a significant increase in cost or complexity.

Another advantage of this device is that apart from providing standoff chemical signatures and analyses of concealed substances, it can simultaneously superimpose the chemical information on top of a normal TV image in a data fusion (or data overlay) approach; that is, an image appears on the screen, the area/subject of interest can be zoomed in on and enlarged and a representation of a chemical spectrum appears on the screen underneath the image. A supplemental technique is also reported upon that, under the appropriate circumstances, enables actual imaging of concealed objects to be accomplished In view of possible terrorist attacks on public areas such as airports, railway and subway stations, sports stadium and the like, it is of paramount importance to be able to detect suspects and suicide bombers before they can detonate their concealed explosives. In addition there is also the need to remotely detect the explosive nature of Improvised Explosive Devices (IEDs) that proliferate both in urban and non-urban settings in recent theatres of combat.

Naturally, it is strategically necessary that such detection be performed remotely in a stand-off way that involves no direct contact with the suspect person or suspect object. In the case of individuals, it is also highly preferable that the subject not be aware that they are being remotely scanned for the possession of explosives (or other contraband).

Line of sight spectroscopy is a mature and well established technique that is effective over great distances, especially if laser-assisted. However, to date line-of-sight spectroscopy has been ineffective in chemically characterising objects at a distance that are not on a surface but are instead concealed by other objects or material such as clothing.

Near-infrared (NIR) spectroscopy is based upon the wavelength-dependent absorption and scattering properties of the object of interest. Both continuous wave systems and those which employ pulses and the various modulation regimes for both, can be used as a probing signal. Presented here is an approach that would have wide application to defence and security issues as it can identify the presence of concealed explosives in response to illumination, providing a repeatable spectral identification. Chemical bonds provide a 'fingerprint' that is based upon the chemical composition of materials under examination.

A method is presented that gives directionality of detection from many meters away and also recovers signal from over 100 dB of noise via NIR Lock In via large scale arrays which produces variations in transmitted intensity and resorts to a totally analogue implementation of the synchronous detection process. Hence, no A/D conversion nor numerical computation, or Digital Signal Processing (DSP) is involved and hence image processing and acquisition times are extremely rapid and in real-time. (See also WO 2008/001141).

The chemical detection capability does not reply solely upon the need to image the object under observation. Instead, an ordinary video image is simultaneously superimposed with a chemical signature that says that the distant person in a crowd (or remote suspect object), also contains within the same field of view, certain chemical compounds.

A supplemental technique is also reported upon that, under the appropriate circumstances, also enables actual imaging of concealed objects to be accomplished.

EXAMPLE 1

Penetration of Clothing by NIR

The ability to penetrate a range of materials such as plastics and fabrics etc is of great use in security screening to uncover concealed objects in-situ. With specific reference to clothing, much use can be made of the fact that almost all clothing is either porous due to an open-weave microstructure or made from fully-dense polymer materials that are actually permeable to NIR in the part of the spectrum between 700 nm to approx 2 μm, as illustrated in FIG. 9 which shows the open microstructure of wool. Cotton and other woven materials, both natural or man-made also have a similar open porosity.

Figure 11:
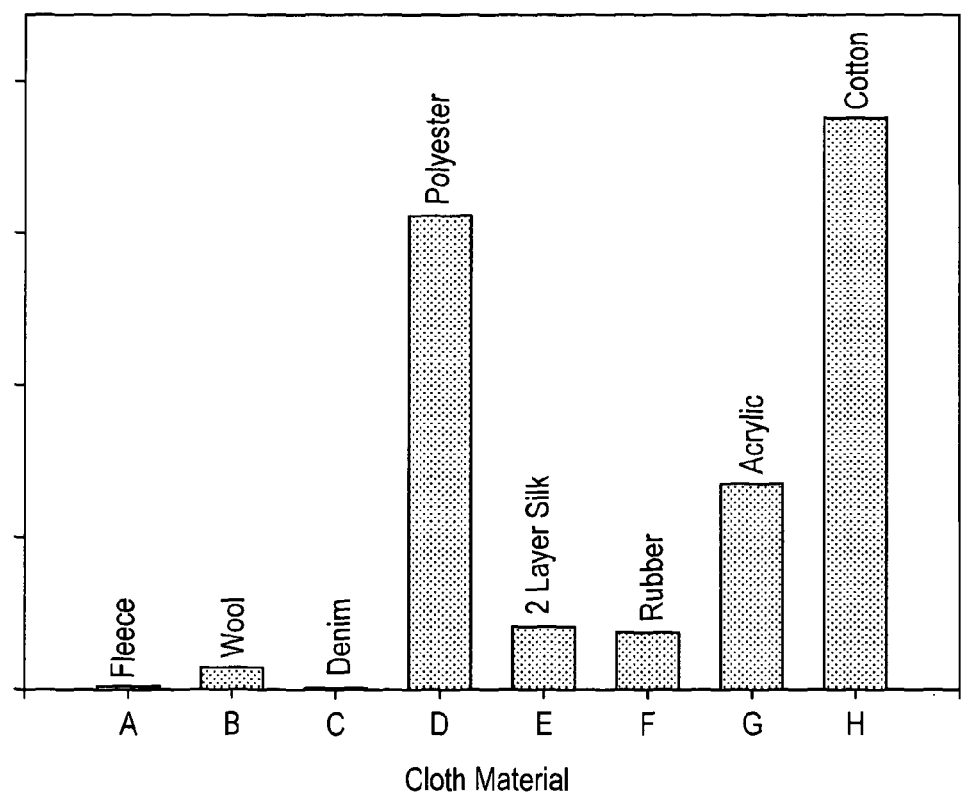
FIG. 11 is a histogram of relative transmission properties of clothing materials to 850 nm radiation showing A) fleece, B) Wool, C) Denim, D) Polyester, E) 2-layer silk, F) Rubber, G) Acrylic and H) Cotton.

FIG. 11 shows a histogram that illustrates the relative straight-line transmission characteristics of 850 nm NIR through single layers of clothing. It more or less indicates that pore size is directly related to weave and openness of the microstructure, with denim admitting far less transmitted light than cotton, for example.

Interestingly, for fully dense materials, pigment tends to have more of an impact and we have, for example, successfully transmitted signals through white leather.

Figure 12:
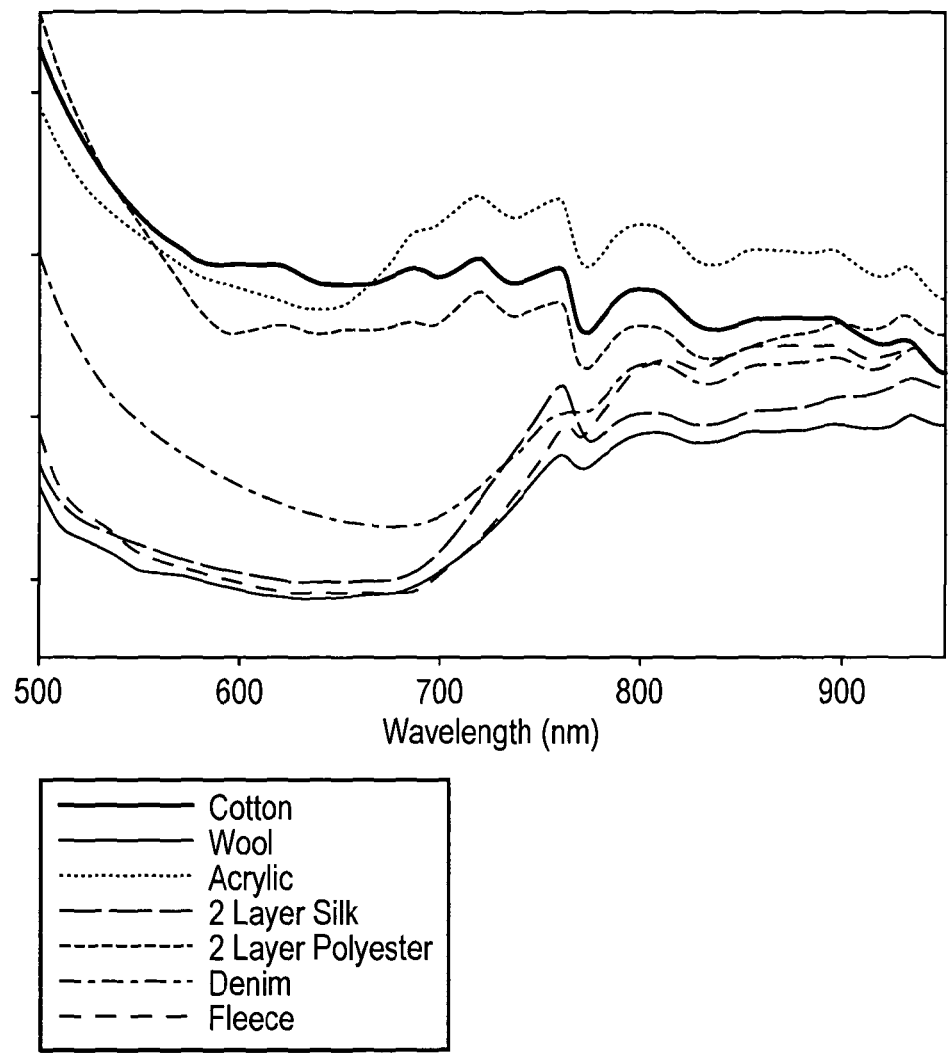
FIG. 12 shows transmission properties of some of the materials of FIG. 10 as a function of wavelength.

The transmission properties for materials across part of the visible/NIR spectral range is illustrated in FIG. 12 and shows the same correlation with microstructure as that of the inline transmission for 850 nm, indicating that it is the microstructure and porosity that dominates in the transmission of light, rather than chemical interaction with the dyes and pigments etc. FIG. 12 also shows that in all cases, sufficient quantities of light are passed in that part of the spectrum necessary to determine key signatures for the common oxidiser and molecular explosives.

The broad modulations versus wavelength in FIG. 12, which seem to be in sympathy for all types of material are instrumentation sensitivity factors. Interestingly enough, towards the NIR end of the spectrum, these patterns dissociate indicating sensitivity to the chemical nature of the clothing and dyes and hence the ability to be sensitive to the detection of other compounds such as explosives.

There are two mechanisms for attenuation of signal—absorption and scattering. As FIG. 12 indicates, for most types of clothing, scattering is by far and away the dominant loss-mechanism. Considering the relative dimensions of pores and fibres and wavelengths, the Mie theory best describes the scattering action of the fibres between these pores.

However, they are not spherical and not of uniform size and distribution and even change when under tension, folded or wet and so calculation of scattering coefficients becomes somewhat problematic. Therefore, direct measurements and empirical trends are used throughout the instrument-design process.

EXAMPLE 2

Signal Attenuation Through Multiple Layers of Clothing

The fact that Mie theory best describes the scattering process is of advantage in the spectroscopic standoff detection of chemicals behind clothing as the process produces a scattering pattern that is more defined and much more intense in the direction of light propagation. The use of NIR at short wavelengths, as opposed to the more traditional longer wavelengths, increases sharpness of this lobe in the forward direction towards the detector.

There is however, one other factor, which is a disadvantage in these measurements and is that that the transmitted intensity drops geometrically when passing through multiple layers of clothing. Basically, at every interface, the pore channels within adjacent layers will not line up exactly with each other, only overlap slightly, or not at all and it is mostly the scattered light from the previous layer which is transmitted through the next.

(Perversely, it only the fact that light is scattered at all that is responsible for the majority of transmission through multiple layers of clothing).

Transmission through multiple layers of clothing is described by an exponential relation between the number of layers and interfaces and final transmitted intensity. In the case of cotton, for most samples which were tried, there was a 70% transmission, i.e. attenuation of −2.9 dB per layer of cotton clothing and this is illustrated by the results presented in FIG. 13 below.

Figure 13A:
FIG. 13 shows a) a plot of amplitude of a transmitted beam as a function of the number of layers of clothing through which the beam is transmitted and b) a logarithmic plot corresponding to that of a)
Figure 13A:
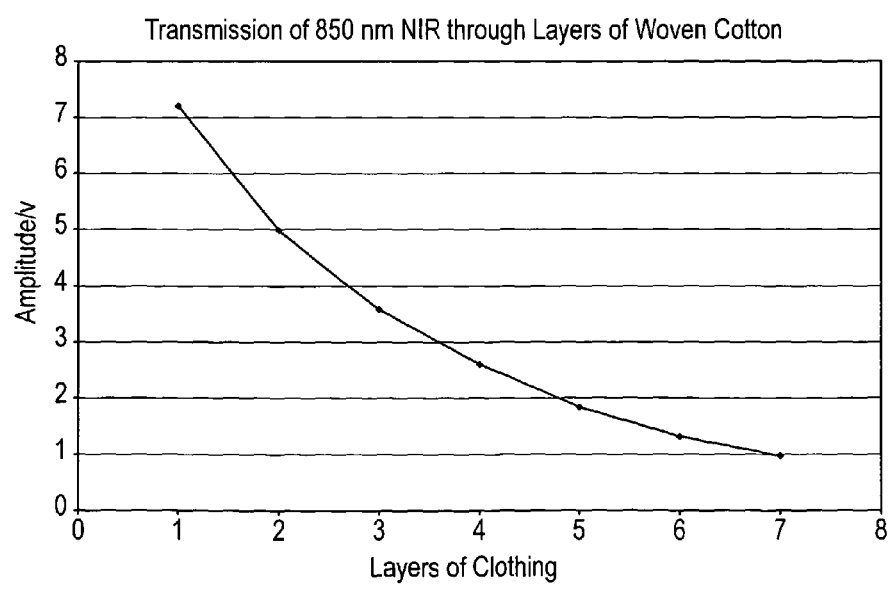

FIG. 13 shows transmission of 850 nm radiation through multiple layers of cotton including material, (a) raw data and (b) Log Plot. As noted above the data shows a 70% transmission—i.e. attenuation is −2.9 dB—per additional layer of cotton clothing

EXAMPLE 3

Spectroscopy of Compounds Concealed by Clothing

NIR wavelengths are capable of chemical bond identification via spectroscopy and this offers the possibility to simultaneously combine chemical/spectral identification with imaging using the Lock-In NIR technique.

Terahertz spectroscopy also has the potential for standoff detection and has the ability to see through some materials that might be used to conceal explosives. However, the development of more powerful sources and atmospheric absorption primarily from water vapour are the primary obstacles for THz spectroscopy [1]. Also as FIG. 14 below illustrates, spectral data from THz techniques is poor at being able to provide chemical discrimination as compared to the visible and NIR part of the spectrum.

Figure 13B:
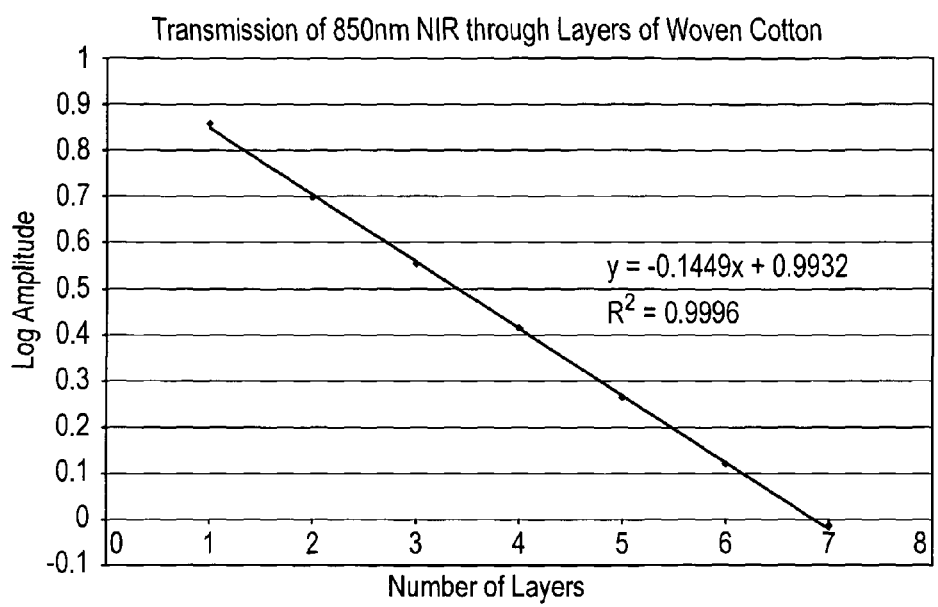
Figure 14A:
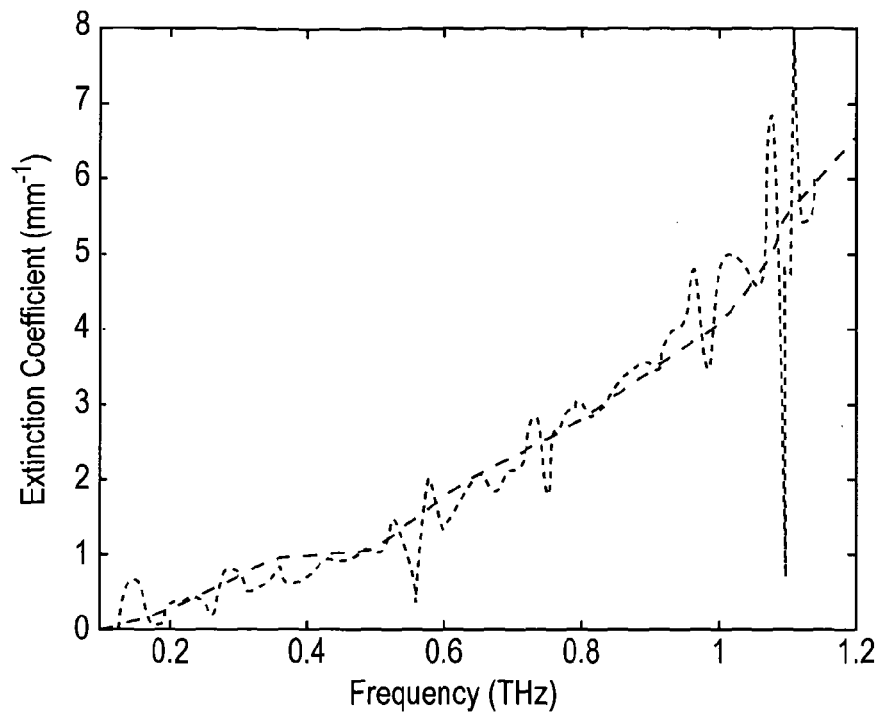
FIG. 14 shows a comparison between the chemical information obtainable from agricultural ammonium nitrate concealed beneath a layer of cotton from a distance of several meters via (a) THz imaging and (b) visible and NIR imaging.
Figure 14B:
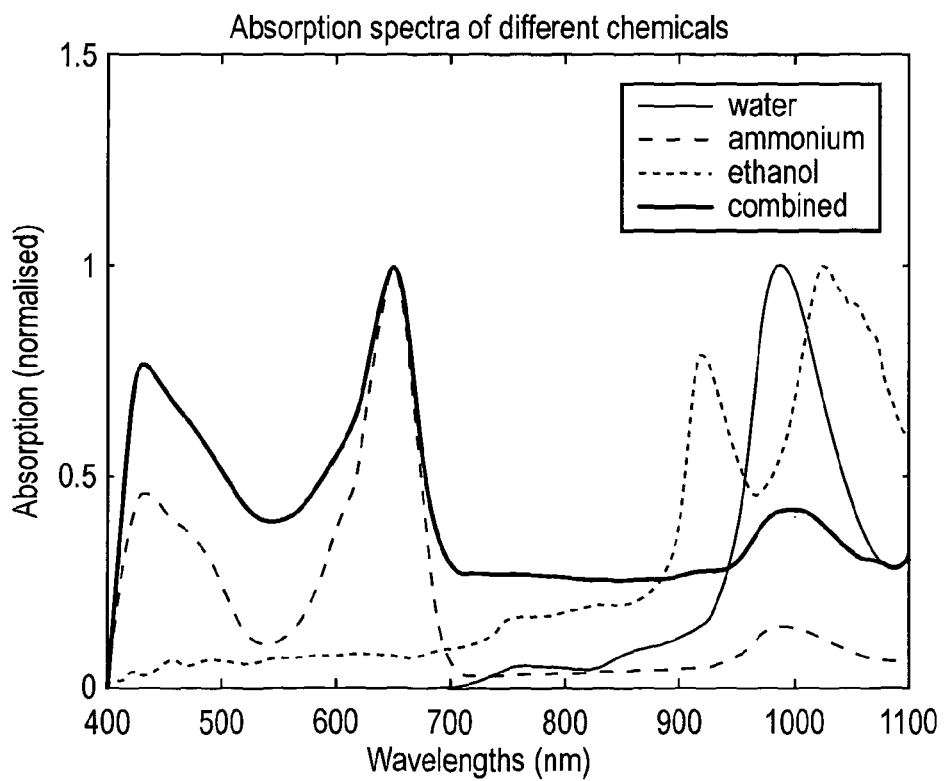

FIG. 14 shows a comparison between the chemical discrimination for the detection of agricultural ammonium nitrate available via THz (FIG. 13(a)) and for visible and NIR (FIG. 13(b)) which was concealed by a layer of cotton from a distance of several meters.

Near infrared (NIR) spectroscopy on the other hand is a very well established technique that has historically been used for many applications, including remote measurements to detect and identify chemical materials. The NIR spectra for explosives for instance—both molecular and oxidiser based—would be OH, CH and NH bonds.

Conventional pyroelectric detectors would be ineffective in this application as their thermal inertia would disallow rapid—real-time imaging and tracking. However, the use of lock-in NIR imaging systems in this part of the spectrum (using very fast bandgap devices as opposed to pyroelectric for the Mid IR) make this possible.

Figure 15:
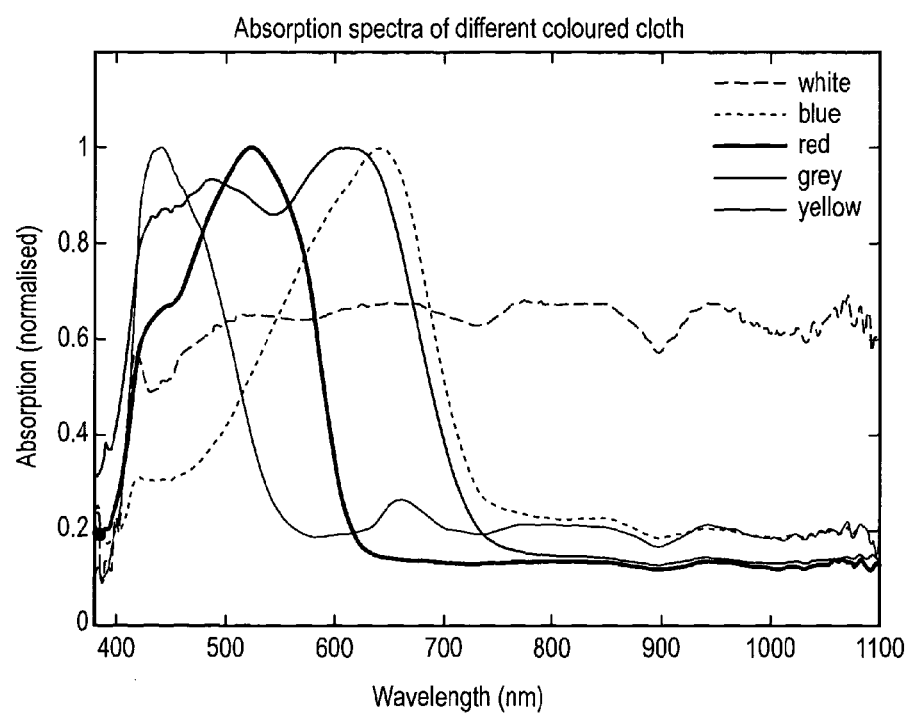
FIG. 15 shows reflectance spectra for a variety of different coloured samples of clothing.

When using reflectance spectroscopy to detect chemicals under clothing on a distant subject, one has to ensure that there will be not be the problem of front-wall reflection contaminating the signal of interest. Fortunately however, another advantage of using NIR is that the reflectance spectrum for most clothes is relatively flat in this part of the spectrum as shown in FIG. 15. FIG. 15 shows reflectance spectra for a variety of different coloured samples of clothing. Note that beyond 800 nm the features are relatively flat and fairly similar.

As has been demonstrated above, because of their porous microstructure, most clothing is permeable to these NIR wavelengths and the two separate features of penetration and standoff chemical analysis, when used in conjunction with the Lock In NIR technique in large area arrays, can then be combined in a data fusion that produces a conventional image with chemical/biological data etc superimposed (e.g. via false colours on the image) by recourse to the appropriate imaging software.

EXAMPLE 4

The Imaging of Concealed Objects Under Clothing

By using the Lock In NIR technique with large-area arrays, the porosity of clothing also affords the means to take images of concealed objects under clothing from several meters away, as is shown if FIG. 16. If only one layer is present too, the scattering is such that the obtained image is very sharp. Should more than one layer be present then anti scattering regimes and protocols (not detailed here) are employed.

FIG. 16(*a*) shows a pair of scissors taped to a chest of a person. FIG. 16(*b*) shows the chest covered in a sweat-shirt concealing the scissors. FIG. 16(*c*) is an image obtained using an embodiment of the invention to image through the sweatshirt. The image shows sharp contrast between the black duct tape A and the black T shirt. Also plainly visible is the blade of the scissors B.

EXAMPLE 5

The Detection of Chemicals Concealed Under Clothing

It must be emphasized that it is not necessary to be able to form an image of a concealed or hidden object in order to be able to perform standoff chemical detection of that object. Diffuse and scattered signals still contain sufficient spectral information necessary for chemical analyses. The diffuse and scattered light, even if reflected back through several layers of clothing may not be able to provide a clear image but will, due to the action of the large area array Lock-In (or similar technique—not detailed here), still be able to retrieve a signal from up to 100 dB of noise.

However, if an object can be imaged underneath clothing, it follows that stand-off chemical analysis may be readily accomplished in some embodiments of the invention.

So mainly, the chemical detection capability does not rely upon the need to image the object under observation. Instead, an ordinary video image is simultaneously superimposed with a chemical signature that says that the distant suspect person in a crowd or remote suspect improvised explosive devices (IEDs) etc also contains within the same field of view certain chemical compounds.

Figure 17A:
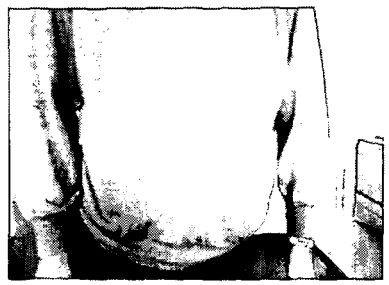
FIG. 17 shows (a) a typical subject having material hidden beneath clothing, and plots of an amount of NIR absorption by the subject as a function of wavelength of the radiation for (b) first and (c) second areas of the subject by standoff chemical analysis from a distance of 5 meters.
Figure 17B:
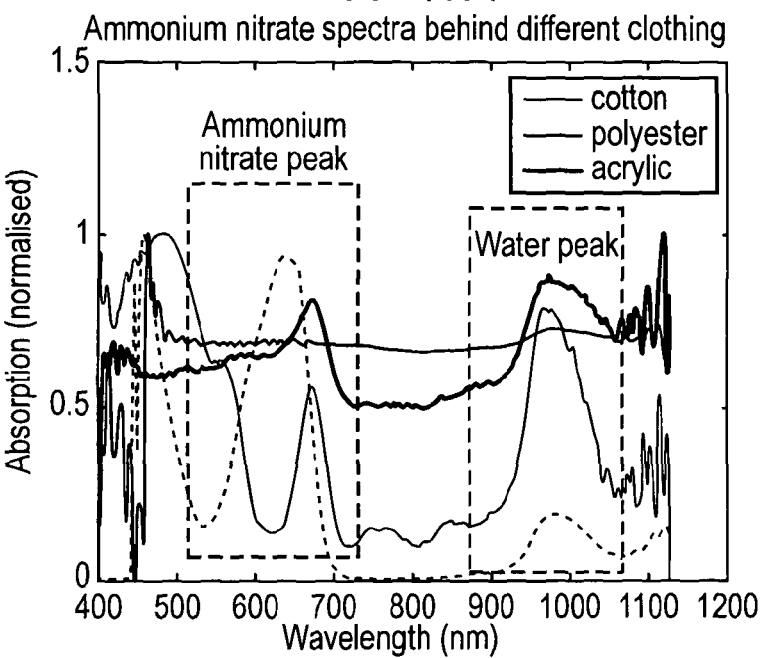
Figure 17C:
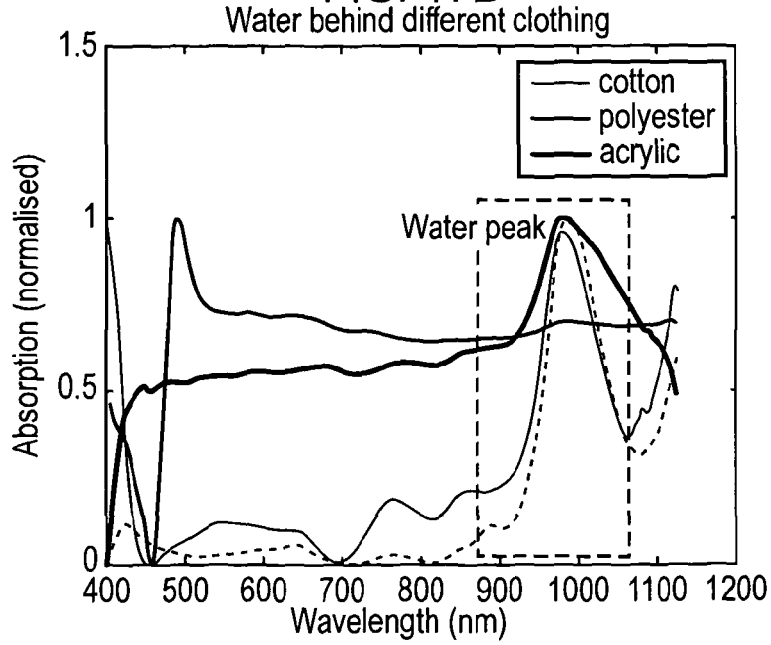

FIG. 17 (*a*) shows a typical subject having material hidden beneath clothing. Initial trials were mostly limited to differentiating between solutions which contained agricultural-grade ammonium fertilizer, which also happens to be the main component of a lot of home-made explosives and IEDs.

FIGS. 17(*b*) and (*c*) are plots of an amount of NIR absorption by the subject as a function of wavelength of the radiation for two different areas of the subject. The results were obtained by standoff chemical analysis a distance of 5 meters.

The plot of FIG. 17(*b*) was obtained from an area of the subject where a solute having ammonium nitrate was concealed and FIG. 17(*c*) was obtained from an area of the subject where a solute not having ammonium nitrate was concealed. It can be seen that peaks in absorption corresponding to ammonium nitrate can be seen in FIG. 17(*b*) and not in FIG. 17(*c*).

Large additional peaks in FIG. 17(*b*) are due to the addition of a chemical dye to off-the shelf ammonium nitrate (fertiliser).

What is clear from inspection of FIG. 17 is the stark difference between the two spectra, clearly indicating the absence and presence of the ammonium nitrate in solution concealed beneath clothing.

Other home-made explosives such as acetone peroxide (TATP) and other oxidiser and nitrate based compounds are easily detectable.

As many optically opaque containers are relatively transparent to NIR wavelengths it is possible to perform accurate chemical analysis of substances in unopened non-metallic containers. Typically, spectroscopic analysis through containers is challenging due to interference from the containers—especially if they are coloured, opaque, or have strong spectral signatures. The benefit of the NIR approach is that it provides a clear chemical spectrum of the contents without any a priori knowledge of the composition of the container.

Given the intrinsically high chemical specificity of NIR spectroscopy, and the ability of NIR wavelengths to penetrate non-metallic containers, some embodiments of the invention are suitable for use in security applications, for example for the inspection of liquids in luggage in airports. Some embodiments permit non-intrusive and rapid detection and chemical analysis of contraband such as drugs and explosives.

To avoid detection via conventional screening and searching techniques, there is a greater incidence in recent times of suicide bombers reportedly strapping explosive devices to their legs and thighs. For this detection application, imaging (and the corresponding chemical analysis) is relatively easy to accomplish, as it only involves one single layer of clothing.

Figure 18:
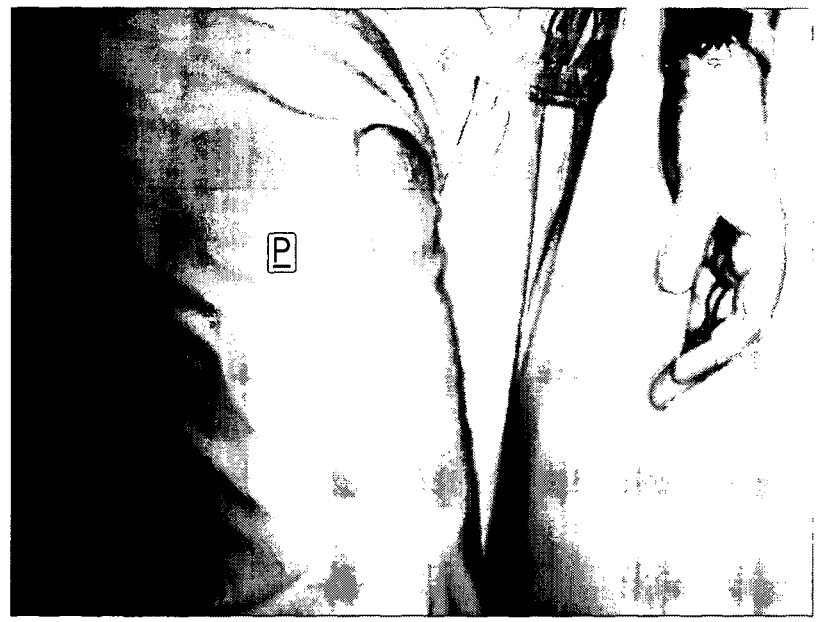
FIG. 18 shows a subject having a package P concealed beneath a trouser leg.
Figure 19:
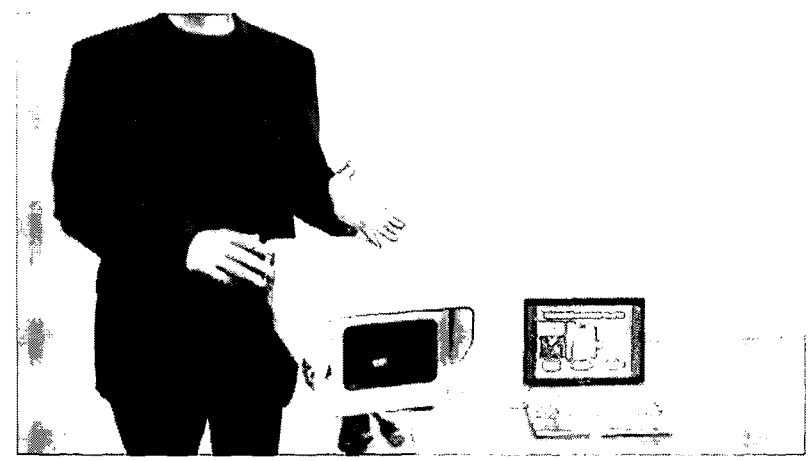
FIG. 19 shows apparatus according to an embodiment of the invention.

FIG. 18 is a still image taken from a real-time movie (10 frames per second) of a subject, who was subject to simultaneous imaging and analysis of a concealed object.

The object concealed under the trousers is held in place by strapping with duct tape to the leg. Sufficient signal for something to be easily imaged means that it is also able to be very easy chemically analysed for explosives or contraband via a stand off NIR technique (see e.g. the apparatus of FIG. 1 to FIG. 8) and variations thereof, or apparatus employing a lock-in technique, see e.g. WO 2008/001141.

Other instances where non-compliant subjects may have hidden articles, weapons or other chemical contraband but whose location and dress can be controlled or are predictable, would be within institutions such as prisons.

A concept demonstrator apparatus is shown in FIG. 18, which integrates the main functions of stand-off detection of explosives hidden under clothing and the spectroscopic analysis of other chemical contraband and IEDs. This information is then overlaid onto conventional imaging pictures of the subject via a data-fusion approach.

In addition, it can also be used in certain situations to obtain actual images of the concealed objects as well, in order to supplement the standoff chemical data also provided.

As noted above, an innovative feature of embodiments of the invention is that the instrument is immune to parallax. In other words, the conventional video image and the spectroscopic analysis are taken from optical signals entering the apparatus on the same optical axis (see FIG. 9 above) regardless of a distance between the camera and the subject of interest.

In some embodiments, the geometric centre of the field of view of a conventional TV image obtained from a camera arranged to receive a beam traveling along the first or second paths 12, 13 corresponds to the portion of the incoming optical signal upon which chemical analysis is performed. The chemical analysis may be performed in some embodiments on the beam traveling along the other of the first or second paths 12, 13.

So for example, in a distant crowd the standoff detection (chemical analysis) may be performed on the one specific suspect zoomed in on in the conventional video (or TV) image (such that that person is at the centre of the video image in the embodiment described above)—and not the person next to him.

Another possible application of apparatus according to embodiments of the invention is the detection of airborne pathogens in public places.

Spectroscopic analysis of organic molecules in the NIR region is dominated by combination and overtone bands of fundamental vibrations that involve aharmonic stretching modes—mainly t O—H, C—H, and N—H bonds. Certain classes of bacteria and spores (such as anthrax and fungal spores too) gives rise to NIR vibrational transitions [2] and thus enable identification of differing strains of pathogen. This analysis would be simpler to accomplish if dealing with bacterial suspensions in liquids or aerosols but might possibly be extended to cover purely airborne contaminants Results of the Lock-In NIR real-time imaging and standoff explosives and chemical detection technique, as used in conjunction with large arrays, successfully demonstrate the principle of being able to chemically analyse and identify explosive material (and potentially other chemical contraband) which was hidden at a distance under clothing.

In principle, this distance could be extended as far as 50 meters without a significant increase in cost or complexity of apparatus according to embodiments of the invention.

Another advantage of this apparatus is that apart from providing standoff chemical signatures and analyses of concealed substances, it can also simultaneously superimpose chemical information on top of a normal TV image in a data fusion approach; that is, an image appears on the screen, the area/subject of interest can be zoomed in on and enlarged and a representation of a chemical spectrum appears on the screen underneath the image.

Parallax is also not a problem. Regardless of how distant the object is from the apparatus, the superposition of chemical data always matches up exactly with the object at the centre of the field of view of the conventional video image.

A supplemental technique is also possible, for use under certain circumstances, that enables the actual imaging of concealed objects to be produced too, as well as its chemical signature.

The technique would appear to produce similar results to those previously thought to be within the exclusive domain of THz systems. The technique may be implemented at reduced cost using 'off-the shelf' components. Apparatus according to embodiments of the invention is inherently far more portable and robust and easy to use; furthermore no special sources of optical radiation are required since commonly available, relatively low cost sources may be used as discussed above.

Apparatus according to embodiments of the invention can also be used over distances of tens of meters without a need for specially controlled environmental conditions of temperature and humidity. The technique has the additional advantage that it enables penetration of wet materials.

Embodiments of the invention are also useful in medical diagnosis, agricultural monitoring, pharmaceutical inspection and industrial quality control etc.

As noted above embodiments of the invention may employ autocorrelation or other lock-in techniques to modulate the source of NIR radiation and recover the signal transmitted from the source through the article under inspection to the detector.

Figure 20:
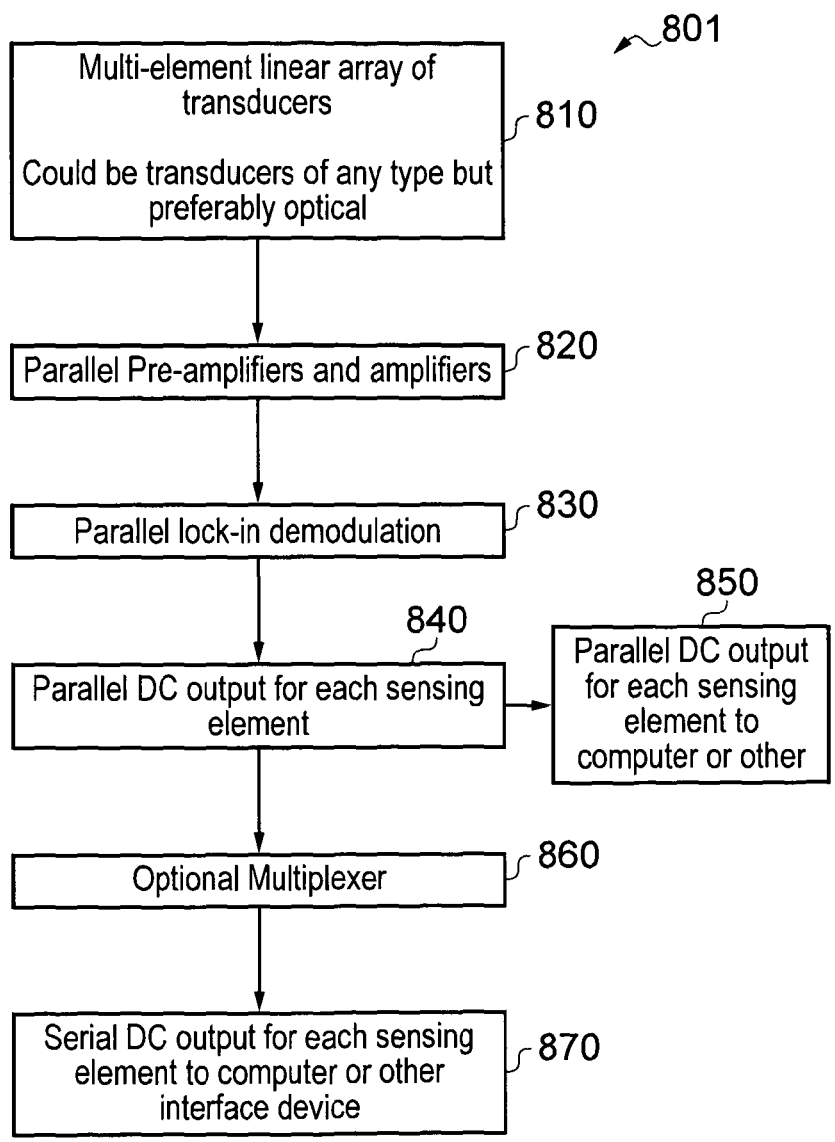
FIG. 20 shows a block diagram of apparatus according to an embodiment of the invention.

The apparatus may employ demodulation apparatus 801 according to an embodiment of the invention as shown in FIG. 20 having an array of photodetectors 810 arranged to detect NIR radiation. In the present example the array 810 is a multi-element linear array. The demodulation apparatus 801 may be employed for demodulating signals from the elements in parallel. It is to be understood that demodulation apparatus according to the present invention may be used with other types of transducer (or detector).

As noted above in one embodiment the array is an array of photodetectors arranged to detect near infra-red (NIR) radiation. More specifically, in some embodiments the array 110 is arranged to detect NIR radiation having a wavelength in the range 700 to 1100 nm. Preferably, the photodetectors are arranged to detect radiation having a wavelength of at least one selected from amongst 850 nm, 980 nm and 1064 nm.

The outputs from the array of transducers is coupled to an input of an amplifier module 820 having a set of parallel pre-amplifiers and amplifiers. The amplifier module 820 is in turn coupled to a parallel lock-in demodulation module 830 arranged to perform demodulation of the input signals in parallel.

The demodulation module 830 is arranged to provide an output 840 corresponding to a demodulated input signal for each of the input signals.

In the embodiment shown the output is in the form of a parallel DC output 850.

Alternatively or in addition, in some embodiments the output may be in the form of a serial output 870 by means of a multiplexer 860.

Figure 21A:
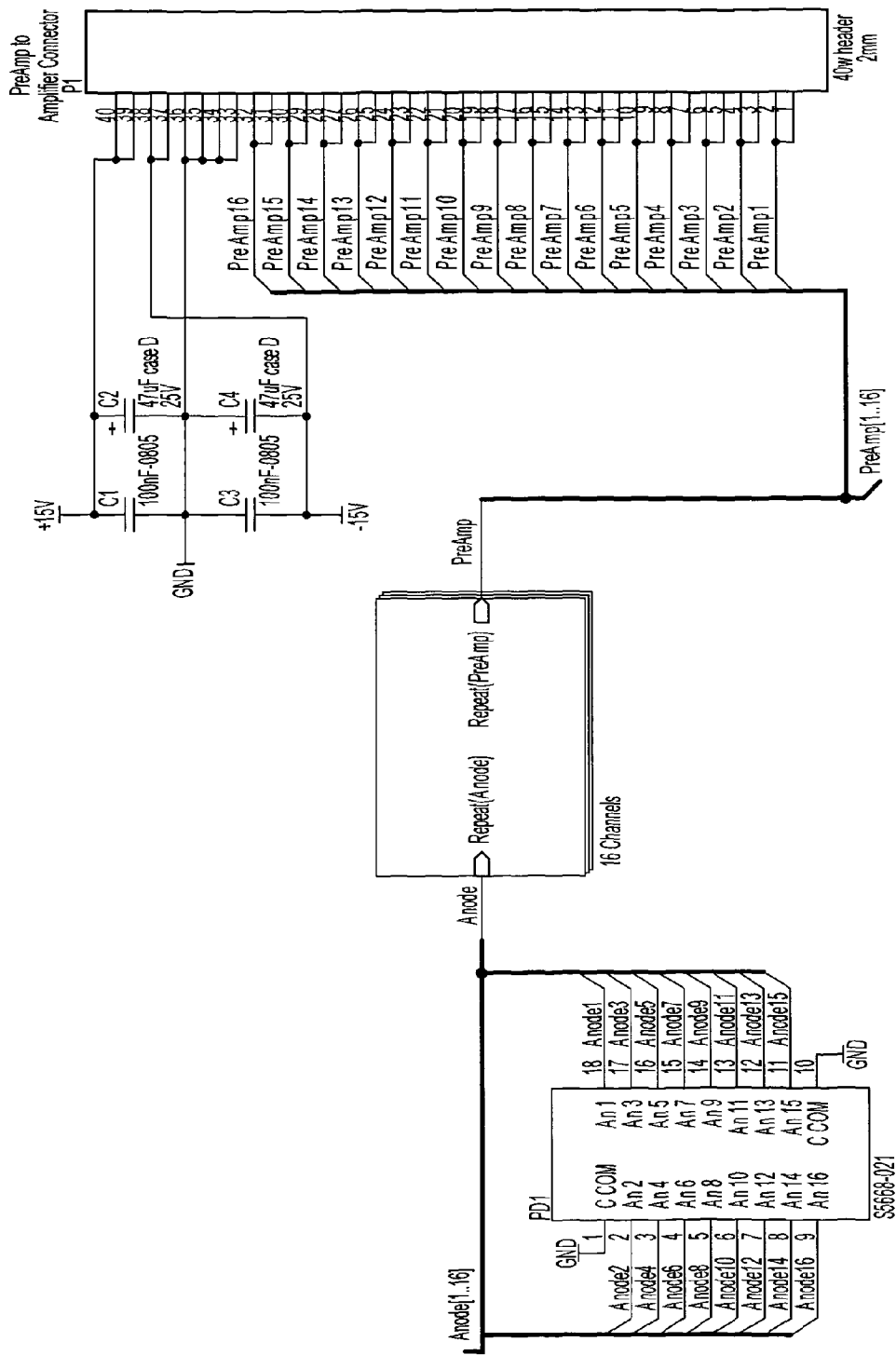
FIG. 21 shows an example of a realisation of portions of the apparatus of FIG. 19.
Figure 21B:
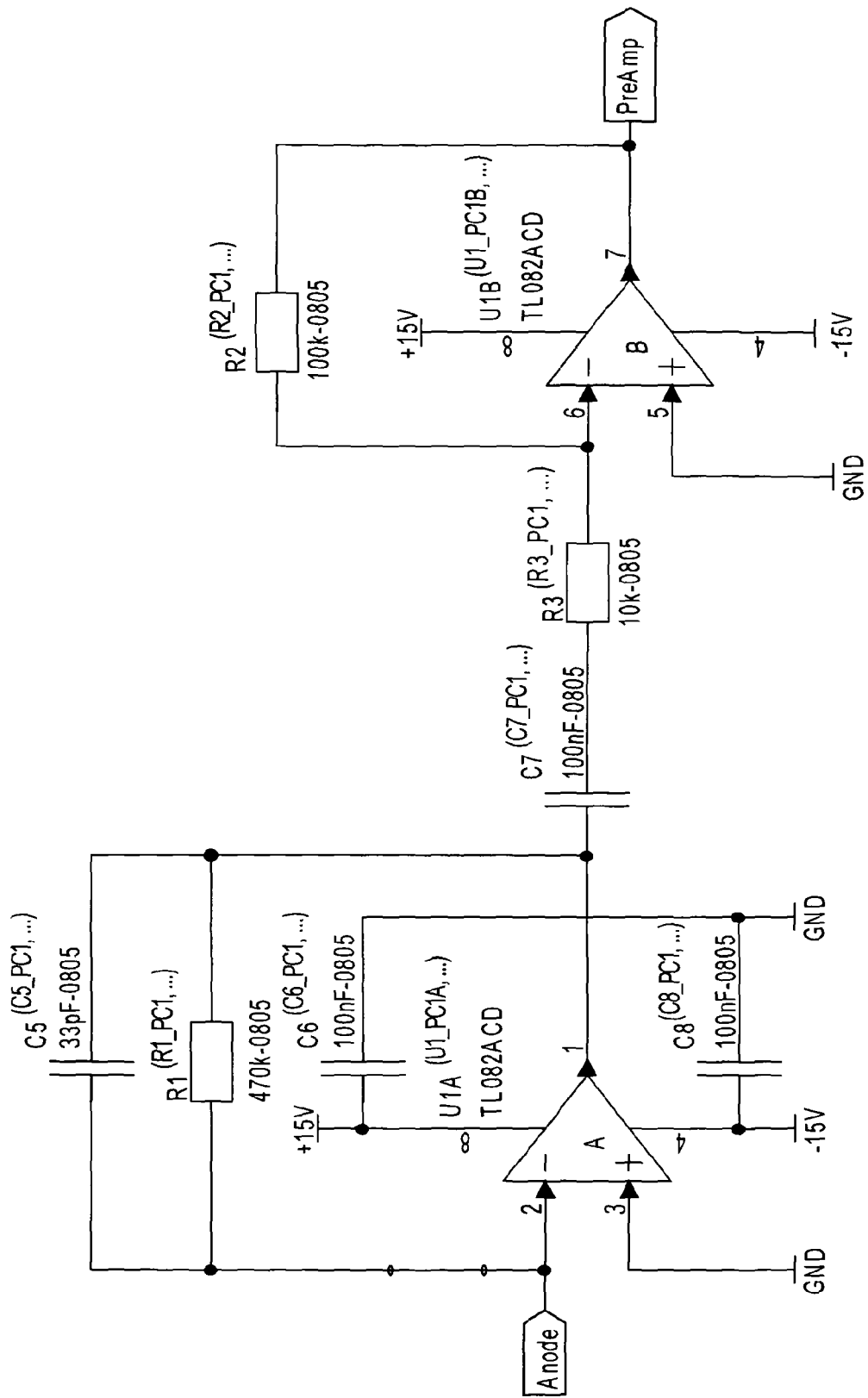
Figure 21C:
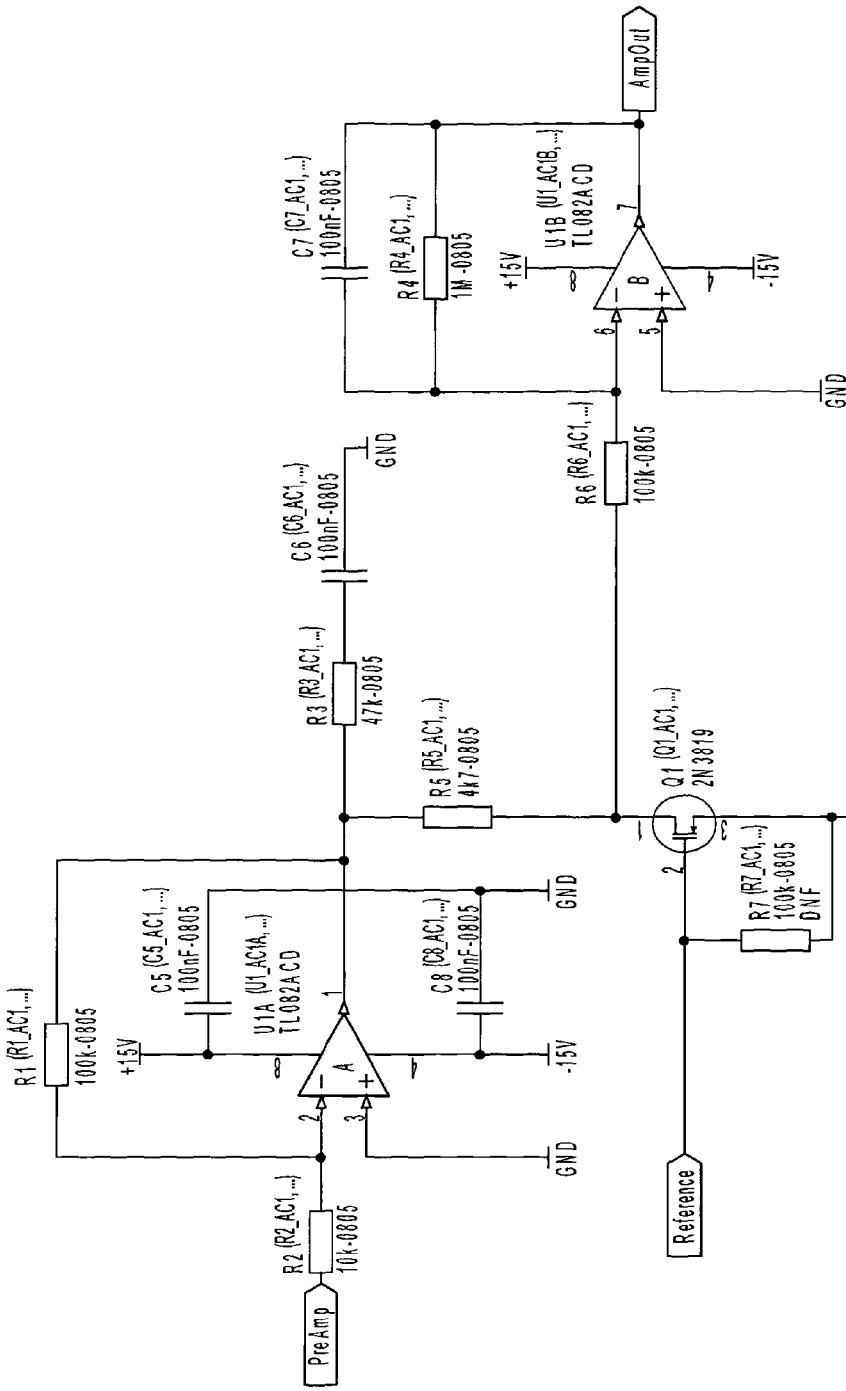

FIG. 21 shows an example of a realisation of portions of the apparatus 801 of FIG. 20. FIG. 21(*a*) is a schematic of a pre-amplifier circuit topsheet; FIG. 21(*b*) is a schematic of a pre-amplifier circuit; and FIG. 21(*c*) is a schematic of an amplifier circuit.

Figure 22:
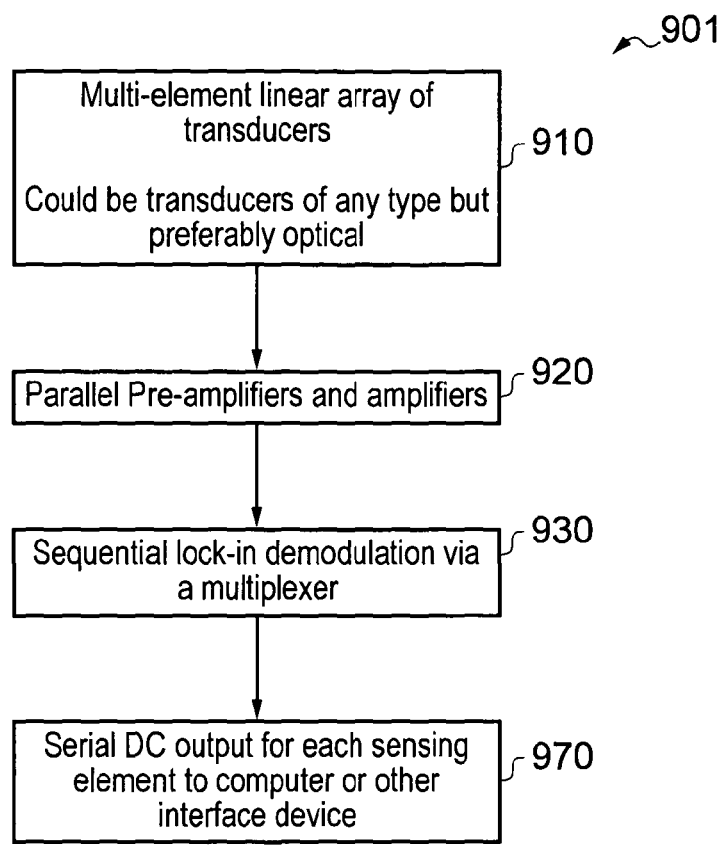
FIG. 22 shows a block diagram of a further apparatus according to an embodiment of the invention.

FIG. 22 shows a block diagram of an alternative apparatus 901 according to an embodiment of the invention.

The apparatus 901 has a multi-element array of transducers similar to that of the embodiment of FIG. 20. An output from each of the transducers is coupled to an input of a corresponding pre-amplifier/amplifier module 920 arranged to pre-amplify and amplify the input signals.

An output from the pre-amplifier/amplifier module 920 is coupled to an input of a sequential lock-in demodulation module 930. The sequential lock-in demodulation module 930 has a multiplexer unit and is arranged to perform sequential lock-in demodulation of the output of the pre-amplifier/amplifier module 920.

The output of the sequential lock-in demodulation module 930 is coupled to a serial DC output module 970 arranged to provide a DC output corresponding to each transducer (or sensing element) in sequence.

It is to be understood that a digital output may be provided in addition or instead of a serial DC output.

Embodiments of the invention may be understood with reference to the following numbered paragraphs:

1. A unit for performing lock-in demodulation of a plurality of input signals comprising:
   an input portion arranged to receive a plurality of input signals;
   a lock-in demodulation portion arranged to demodulate the plurality of input signals; and
   an output portion arranged to provide a plurality of output signals corresponding to each of the demodulated input signals.

2. A unit as described in paragraph 1 wherein the lock-in demodulation portion comprises a parallel lock-in demodulation portion.

3. A unit as described in paragraph 2 wherein the parallel lock-in demodulation portion is arranged to perform lock-in demodulation of a plurality of input signals substantially simultaneously.

4. A unit as described in any preceding paragraph wherein the lock-in demodulation portion comprises a serial lock-in demodulation portion.

5. A unit as described in paragraph 4 wherein the serial lock-in demodulation portion is arranged to perform lock-in demodulation of a plurality of input signals substantially sequentially.

6. A unit as described in any preceding paragraph wherein the input portion comprises a plurality of input signal lines each line being arranged to receive at least one of the plurality of input signals.

7. A unit as described in paragraph 6 wherein the number of input signal lines corresponds to the number of input signals.

8. A unit as described in paragraph 7 wherein the number of input signal lines is substantially equal to the number of input signals.

9. A unit as described in any preceding paragraph wherein the output portion comprises a plurality of output signal lines each line being arranged to provide at least one of the plurality of output signals.

10. A unit as described in paragraph 9 wherein the number of output signal lines corresponds to the number of output signals.

11. A unit as described in paragraph 10 wherein the number of output signal lines is substantially equal to the number of output signals.

12. A unit as described in any preceding paragraph wherein the output portion comprises a multiplexer arranged to provide a serial output of the output signals.

13. A unit as described in any preceding paragraph wherein the input portion is coupled to a plurality of transducers, each transducer being arranged to provide an input signal to the unit.

14. A unit as described in paragraph 13 wherein the plurality of transducers are arranged in an array.

15. A unit as described in paragraph 14 wherein the array is one selected from amongst a one dimensional array, a two dimensional array and a three dimensional array.

16. A unit as described in any one of paragraphs 13 to 15 wherein the transducers comprise at least one selected from amongst an audio transducer, an optical detector, an electromagnetic detector, an electrostatic detectors and a strain gauge.

17. A method of performing lock-in demodulation of a plurality of input signals comprising:
    receiving at an input portion a plurality of input signals;
    performing a lock-in demodulation process thereby to demodulate the plurality of input signals; and
    outputting at an output a plurality of output signals corresponding to each of the demodulated input signals.

18. A method as described in paragraph 17 wherein performing a lock-in demodulation process comprises the step of performing a parallel lock-in demodulation process.

19. A method as described in paragraph 18 wherein the step of performing a parallel lock-in demodulation process comprises performing lock-in demodulation of a plurality of input signals substantially simultaneously.

20. A method as described in any one of paragraphs 17 to 19 wherein the step of performing a lock-in demodulation process comprises performing a serial lock-in demodulation process.

21. A method as described in paragraph 20 wherein the step of performing a serial lock-in demodulation process comprises the step of performing a lock-in demodulation of the plurality of input signals substantially sequentially.

22. A method as described in any one of paragraphs 17 to 21 wherein the step of receiving the plurality of input signals comprises the step of receiving the plurality of input signals via a plurality of input signal lines each line being arranged to receive at least one of the plurality of input signals.

23. A method as described in paragraph 22 comprising the step of receiving each input signal via a different respective input signal line.

24. A method as described in any one of paragraphs 17 to 23 wherein the step of outputting at an output a plurality of output signals corresponding to each of the demodulated input signals comprise outputting the output signals to a plurality of output signal lines each line being arranged to provide at least one of the plurality of output signals.

25. A method as described in any one of paragraphs 17 to 24 comprising the step outputting the output signals in a serial manner.

26. A method as described in any one of paragraphs 17 to 25 comprising the step outputting the output signals in a serial manner through a single output signal line.

27. A method as described in any one of paragraphs 17 to 26 comprising the step of obtaining each of the input signals from a transducer.

28. A method as described in paragraph 27 wherein the transducers are arranged in an array.

29. A method as described in paragraph 27 wherein the transducers are arranged in an array being one selected from amongst a one dimensional array, a two dimensional array and a three dimensional array.

30. A method as described in any one of paragraphs 27 to 29 comprising the step of detecting by means of one of the transducers at least one selected from amongst an audio signal, an optical signal, an electromagnetic signal, an electrostatic signal and a strain signal.

31. A unit for performing parallel lock-in demodulation comprising:
    an input portion arranged to receive a plurality of input signals;
    a parallel lock-in demodulation portion arranged to demodulate the plurality of input signals; and
    an output portion arranged to provide a plurality of output signals corresponding to each of the demodulated input signals.

32. A unit for performing lock-in demodulation of a plurality of input signals comprising:
    an input portion arranged to receive a plurality of input signals;
    a sequential lock-in demodulation portion arranged to demodulate the plurality of input signals; and
    an output portion arranged to provide a plurality of output signals corresponding to each of the demodulated input signals.

REFERENCES

[1] Adrian Dobroiu1, Chiko Otani and Kodo Kawase1, "Terahertz-wave sources and imaging Applications" Meas. Sci. Technol. 17 (2006) R161-R174

[2] L. E. Rodriguez-Saona, F. M. Khambaty, F. S. Fry, and E. M. Calvey "Rapid Detection and Identification of Bacterial Strains by Fourier Transform Near—Infrared Spectroscopy" J. Agric. Food Chem. (2001), 49, 574-579

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. Apparatus for detecting a concealed object in an article comprising:
    a source of Near Infra-Red (NIR) radiation operable to illuminate an article to be inspected;
    a detector, the detector being configured to detect that portion of the source beam incident on the detector that has been passed through at least a portion of the article;
    a collimator, the collimator having an entrance aperture, the collimator being arranged to collimate light passing through the entrance aperture that has passed through the article before it reaches the detector; and
    control means for detecting by means of the detector an intensity of NIR illumination incident on the detector and to identify the presence of a concealed object in an article responsive to a variation in detected intensity across at least a portion of the article,
    wherein the control means is arranged to detect a concealed object not by imaging nor by a single point measurement or single measurement of the integrated total transmitted radiation through the whole of the object but by evaluation of the whole of the article with reference to variances in transmitted radiation through a least part of an article but without spatial reference to said least part of the article; and
    wherein the detector comprises a plurality of photodetectors, respective photodetectors having an optic axis substantially coincident with an optic axis of a corresponding source element.

2. Apparatus of claim 1 wherein the detector comprises an elongate detector.

3. Apparatus of claim 1 comprising a diffuser arranged to scatter light from the source onto the sample thereby to illuminate diffusely the sample.

4. Apparatus of claim 1 wherein the source comprises a plurality of light emitting elements at different respective spatial locations.

5. Apparatus of claim 4 wherein the source illuminates at least one but not all of the source elements and the detector detects by means of detector light incident thereon from the at least one illuminated source element at a plurality of different spatial locations.

6. Apparatus of claim 1 wherein the detector comprises a plurality of photo-detector elements, the detector being operable to output respective values of intensity of NIR radiation incident upon the elements.

7. Apparatus of claim 1 wherein the source illuminates the article singly from a plurality of light emitting elements at different respective spatial locations, and the illumination spot falling upon the article is very much smaller than the desired minimum size of detection of the concealed object so as to maximize effectiveness of detection of said concealed object.

8. Apparatus of claim 1 wherein the control means analyzes histogram distributions of transmitted radiation intensities through a least part of an article but without reference to the spatial coordinates of said least part of the article as a means of detecting objects concealed within the article without an intention or requirement to generate an image of the article or portion thereof.

9. Apparatus of claim 1 wherein the control means is operable to illuminate each source element in turn and the detector detects by means of the detector light incident thereon from each respective source element in turn at a plurality of different spatial locations.

10. Apparatus of claim 1 wherein the control means is operable to illuminate each source element in turn and the detector detects by means of the detector light incident thereon from each respective source element in turn at a position of the detector corresponding substantially to a substantially direct path of NIR radiation from each detector through the article.

11. Apparatus of claim 1 wherein the detector comprises one selected from amongst a linear D array of photodetector elements and a 2D array of photodetector elements.

12. Apparatus of claim 1 wherein the source is arranged to direct the radiation to pass through a conveyor as it passes from the source to the detector.

13. Apparatus of claim 1 wherein the source is operable to irradiate the sample with polarized radiation and the detector is configured to detect a change in polarization of the radiation by the sample.

14. Apparatus of claim 1 wherein a signal from the detector corresponding to the intensity of NIR incident thereon is subject to logarithmic amplification whereby an amount of amplification of a signal decreases as a function of signal amplitude according to a logarithmic relationship.

15. Apparatus of claim 1 comprising a beam splitter and at least two detectors, the beam splitter being arranged to split the beam transmitted through the sample and to direct respective split portions of the beam to a respective one of the at least two detectors.

16. Apparatus of claim 15 wherein one of the at least two detectors is configured to detect visible radiation.

17. Apparatus of claim 16 wherein said one of the at least two detectors in is configured to form an image of the article.

18. Apparatus of claim 15 wherein one of the at least two detectors is arranged to detect NIR radiation of a first frequency and not a second frequency and another of the detectors is arranged to detect NIR radiation of the second frequency and not the first frequency, and wherein detection is enhanced by an analysis of the difference in the transmitted intensities of each separate frequency.

19. Apparatus of claim 15 wherein at least one of the two detectors comprises a spectrometer arranged to provide a signal responsive to an intensity of radiation of a given frequency as a function of frequency.

* * * * *